United States Patent de Laszlo et al.

Patent Number: 5,385,894
Date of Patent: Jan. 31, 1995

[54] DISUBSTITUTED 6-AMINOQUINAZOLINONES

[75] Inventors: Stephen E. de Laszlo, Atlantic Highlands; Tomasz W. Glinka, Scotch Plains; William J. Greenlee, Teaneck; Prasun K. Chakravarty, Edison; Arthur A. Patchett, Westfield, all of N.J.

[73] Assignee: Merck & Co., Inc., Rahway, N.J.

[21] Appl. No.: 222,354

[22] Filed: Apr. 4, 1994

Related U.S. Application Data

[63] Continuation of Ser. No. 912,458, Jul. 13, 1992, abandoned, which is a continuation-in-part of Ser. No. 665,389, Mar. 6, 1991, abandoned.

[51] Int. Cl.⁶ ............... A61K 31/505; C07D 403/10; C07D 239/91
[52] U.S. Cl. .................. 514/80; 514/259; 514/253; 514/234.5; 544/244; 544/284; 544/287; 544/283; 544/116; 544/289
[58] Field of Search ............ 544/283, 284, 287, 289, 544/116, 244; 514/253, 259, 234.5, 80

[56] References Cited

U.S. PATENT DOCUMENTS

| | | | |
|---|---|---|---|
| 5,162,325 | 11/1992 | Chakravarty | 514/259 |
| 5,166,206 | 11/1992 | Allen et al. | 514/269 |
| 5,240,928 | 8/1993 | Allen et al. | 514/259 |
| 5,290,780 | 3/1994 | Venkatesan et al. | 519/259 |

FOREIGN PATENT DOCUMENTS

| | | |
|---|---|---|
| 58696/90 | 1/1991 | Australia . |
| 253310 | 1/1988 | European Pat. Off. . |
| 411766 | 2/1991 | European Pat. Off. . |
| 445811 | 9/1991 | European Pat. Off. . |

OTHER PUBLICATIONS

Wong et al., *Eur. J. Pharmacol.*, 202, 323–330 (1991).

*Primary Examiner*—Mukund J. Shah
*Assistant Examiner*—Matthew V. Grumbling
*Attorney, Agent, or Firm*—Valerie J. Camara; Mark R. Daniel; Joseph F. DiPrima

[57] ABSTRACT

Novel disubstituted 6-aminoquinazolinones of the Formula (I), are useful as angiotensin II antagonists:

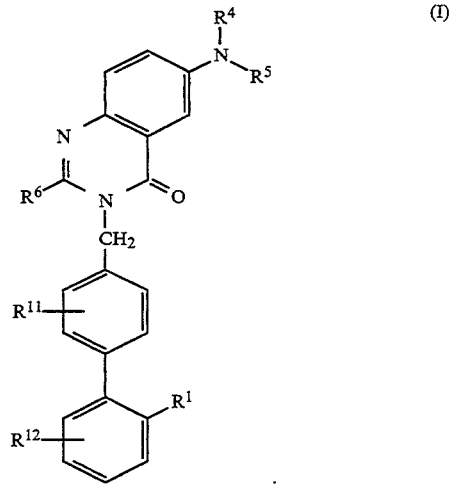

5 Claims, No Drawings

DISUBSTITUTED 6-AMINOQUINAZOLINONES

INTRODUCTION OF THE INVENTION

This is a continuation of application Ser. No. 07/912,458 filed on Jul. 13, 1992 now abandoned which is a continuation-in-part of copending application Ser. No. 07/665,389, filed Mar. 6, 1991 now abandoned.

This invention relates to novel disubstituted 6-aminoquinazolinone compounds and derivatives thereof which are useful as angiotensin II antagonists in the treatment of elevated blood pressure, congestive heart failure and ocular hypertension. Thus, the disubstituted 6-aminoquinazolinone compounds of the invention are useful as antihypertensives.

It also relates to processes for preparing the novel compounds; pharmaceutical formulations comprising one or more of the compounds as active ingredient; and a method of treatment of hypertension, congestive heart failure, and elevated intraocular pressure.

The compounds of this invention also exhibit central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

Further, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during, the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs,* ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; and 291,969; and in articles by A. T. Chiu, et al. [*Eur. J. Pharm. Exp. Therap,* 157, 13–21 (1988)] and by P. C. Wong, et al. [*J. Pharm. Exp. Therap,* 247, 1–7(1988), *Hypertension,* 13, 489–497 (1989)]. All of the U.S. Patents, European Patent Applications 028,834, 253,310, 399,731 and 400,974 and the two articles disclose substituted imidazole compounds which are generally bonded through a lower alkyl bridge to a substituted phenyl.

DETAILED DESCRIPTION OF THE INVENTION

This invention relates to novel disubstituted 6-aminoquinazolinone compounds and derivatives thereof which are useful as nonselective angiotensin II antagonists, as antihypertensives, in the treatment of congestive heart failure and in the treatment of elevated intraocular pressure. The compounds of this invention have the general formula (I):

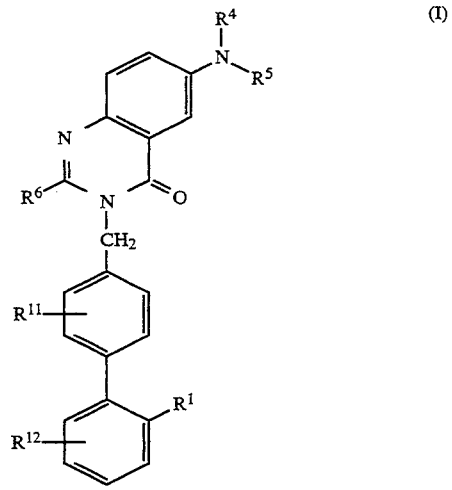

or a pharmaceutically acceptable salt thereof, wherein:

$R^1$ is
 (a) $CO_2R^2$,
 (b) tetrazol-5-yl,
 (c) $NHSO_2CF_3$,
 (d) $SO_2NHCOR^3$, or
 (e) $SO_2NH$-heteroaryl;

$R^2$ is
 (a) hydrogen, or
 (b) $C_1-C_6$ alkyl;

$R^3$ is
 (a) $C_1-C_6$ alkyl,
 (b) $C_3-C_7$ cycloalkyl,
 (c) phenyl,
 (d) substituted phenyl in which the substituent is F, Cl, Br, $C_1-C_4$ alkoxy, perfluoro $C_1-C_4$ alkyl, di-($C_1-C_4$-alkyl)amino, or $CO_2R^2$,
 (e) substituted $C_1-C_8$ alkyl in which the substituent is $C_3-C_7$ cycloalkyl, $C_1-C_4$ alkoxy, hydroxy, di-($C_1-C_4$ alkyl)amino, $CO_2R^2$, morpholinyl, $C_1-C_4$ alkylpiperazinyl, $CF_3$, thio, $C_1-C_4$ alkylsulfinyl, $C_1-C_4$ alkylsulfonyl, heteroaryl, $NH_2$, or aryl, or
 (f) heteroaryl;

$R^4$ is
 (a) $C_1-C_6$ alkyl,
 (b) substituted $C_1-C_6$ alkyl in which the substituent is $C_3-C_7$ cycloalkyl, $C_1-C_4$ alkoxy, hydroxy, di-($C_1-C_4$ alkyl)amino, $CO_2R^2$, morpholinyl, $C_1-C_4$ alkylpiperazinyl, $CF_3$, $C_1-C_4$ alkylthio, $C_1-C_4$ alkylsulfinyl, $C_1$-$C_4$ alkylsulfonyl, —CHO, $O(C_2$-$C_3$ alkyl-O—$)_n$ $C_1$-$C_3$ alkyl where n=1-5, or $NHCO_2(C_1$-$C_6$-alkyl).

(c) $C_2$-$C_6$ alkenyl,
(d) phenyl $C_1$-$C_6$ alkyl,
(e) substituted phenyl $C_1$-$C_6$ alkyl, in which the substituent on the phenyl group is hydroxy, $C_1$-$C_4$ alkoxy, F, Cl, I, Br, $NO_2$, cyano, $CO_2R^2$, di($C_1$-$C_4$alkyl)amino, —Obenzyl, $CF_3$, phenyl-$C_1$-$C_4$-alkoxy, $C_1$-$C_4$ alkylthio, $C_1$-$C_4$-alkylsulfinyl, —OPO(O-benzyl)$_2$, or $C_1$-$C_4$ alkylsulfonyl, amino, P(O)(OH)$_2$, $C_1$-$C_4$ alkyl, —OPO(O—$C_1$-$C_6$ alkyl)$_2$, OPO(OH)$_2$, OCO(CH$_2$)$_2$COOH, OSO$_3$H, or O($C_2$-$C_3$alkyl-O—$)_n$ $C_1$-$C_3$ alkyl,
(f) heteroaryl $C_1$-$C_6$ alkyl, or
(g) substituted heteroaryl $C_1$-$C_6$ alkyl, in which the substituent on the heteroaryl group is F, Cl, $NO_2$, $CO_2R^2$, or di-($C_1$-$C_4$ alkyl)amino;

$R^5$ is
(a) $CO_2R^7$,
(b) $CONR^8R^9$,
(c) $COR^{10}$,
(d) $SO_2NR^8R^9$, or
(e) $SO_2R^{10}$;

$R^6$ is
(a) $C_1$-$C_6$ alkyl,
(b) substituted $C_1$-$C_6$ alkyl in which the substituent is $C_3$-$C_7$ cycloalkyl, benzyl or $C_1$-$C_4$-alkoxy,
(c) cyclopropyl;

$R^7$ is
(a) $C_1$-$C_6$ alkyl,
(b) substituted $C_1$-$C_6$ alkyl in which the substituent is $C_1$-$C_4$ alkoxy, hydroxy, di($C_1$-$C_4$ alkyl)amino, $CO_2R^2$, morpholinyl, $C_1$-$C_4$ alkylpiperazinyl, $C_1$-$C_4$ alkylsulfinyl, $C_1$-$C_4$ alkylsulfonyl, or O($C_2$-$C_3$alkyl-O—$)_n$ $C_1$-$C_3$ alkyl,
(c) phenyl $C_1$-$C_6$ alkyl,
(d) substituted phenyl $C_1$-$C_6$ alkyl, in which the substituent on the phenyl group is hydroxy, $C_1$-$C_4$ alkoxy, F, Cl, $NO_2$, cyano, $CO_2R_2$, di($C_1$-$C_4$alkyl)amino, $CF_3$, phenyl $C_1$-$C_4$ alkoxy, $C_1$-$C_4$ alkylthio, $C_1$-$C_4$ alkylsulfinyl, $C_1$-$C_4$ alkylsulfonyl, or O($C_2$-$C_3$alkyl-O—$)_n$ $C_1$-$C_3$ alkyl,
(e) heteroaryl $C_1$-$C_6$ alkyl, or
(f) substituted heteroaryl $C_1$-$C_6$ alkyl, in which the substituent on the heteroaryl group is F, Cl, $NO_2$, $CO_2R^2$, or di-($C_1$-$C_4$ alkyl)amino;

$R^8$ is
(a) hydrogen, or
(b) $C_1$-$C_6$ alkyl;

$R^9$ is
(a) $C_1$-$C_6$ alkyl, or
(b) substituted $C_1$-$C_6$ alkyl in which the substituent is $C_1$-$C_4$ alkoxy, hydroxy, di-($C_1$-$C_4$ alkyl)amino, $CO_2R^2$, morpholinyl, $C_1$-$C_4$ alkylpiperazinyl, $C_1$-$C_4$ alkylsulfinyl or $C_1$-$C_4$ alkylsulfonyl,
(c) perfluoro $C_1$-$C_6$ alkyl,
(d) phenyl,
(e) heteroaryl, or $R^8$ and $R^9$ taken together are morpholino,

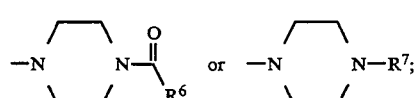

$R^{10}$ is (a) phenyl,
(b) substituted phenyl in which the substituent is F, Cl, Br, I, $C_1$-$C_4$-alkoxy, $C_1$-$C_4$ alkyl, $NO_2$, cyano, $OC_6H_5$, $CO_2R^2$, di($C_1$-$C_4$ alkylamino), $CF_3$, $C_1$-$C_4$ alkylthio, $C_1$-$C_4$ alkylsulfinyl, $C_1$-$C_4$ alkylsulfonyl, —OPO(O$C_1$-$C_6$-alkyl)$_2$, OPO(OH)$_2$, OPO(O-benzyl)$_2$, OCO(CH$_2$)$_2$COOH, OSO$_2$OH, —PO(O$C_1$-$C_6$- alkyl)$_2$, —PO(OH)$_2$, OBn, or O-($C_2$-$C_3$alkyl-O)$_n$ $C_1$-$C_3$ alkyl,
(c) phenyl $C_1$-$C_6$ alkyl,
(d) heteroaryl,
(e) $C_1$-$C_6$ alkyl,
(f) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, thio, $C_1$-$C_4$ alkylsulfinyl, $C_1$-$C_4$ alkylsulfonyl, imidazolyl, —N(CO$C_1$-$C_6$ alkyl)piperazinyl, or N-aryl-piperazinyl,
(g) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-$C_4$alkyl)amino, $CF_3$, phenyl $C_1$-$C_4$ alkoxy, thio, $C_1$-$C_4$ alkylsulfinyl, or $C_1$-$C_4$-alkylsulfonyl, or
(h) $C_{3-7}$ cycloalkyl.

$R^{11}$ is
(a) hydrogen,
(b) F, Cl, Br or I
(c) $C_1$-$C_4$ alkyl,
(d) $C_1$-$C_4$ alkoxy, $R^{12}$ is
(a) hydrogen,
(b) $C_1$-$C_5$ alkyl,
(c) phenyl,
(d) substituted phenyl in which the substituent is $C_1$-$C_4$ alkoxy, F, Cl, $CO_2R^2$, di($C_1$-$C_4$alkyl)amino, thio, $C_1$-$C_4$ alkylsulfinyl, $C_1$-$C_4$ alkylsulfonyl.

The term heteroaryl is an unsubstituted, monosubstituted or disubstituted five or six membered aromatic ring which contains 1 to 3 heteroatoms selected from O, S, or N and the substituents are selected from the group consisting of $C_1$-$C_4$ alkyl, F, Cl, $CO_2R^2$, or di-($C_1$-$C_4$ alkyl)amino.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The abbreviations defined in the table below are used in the specific embodiments which are illustrated in tabular form:

| Table of abbreviations | | | |
|---|---|---|---|
| Me | methyl | iPn | isopentyl |
| Et | ethyl | Hx/Hex | n-hexyl |
| Pr | n-propyl | chex | cyclohexyl |
| iPr | isopropyl | Boc | butyloxycarbonyl |
| cPr | cyclopropyl | Ph | phenyl |
| Bu | n-butyl | BHn | benzyl |
| iBu | isobutyl | Bz | benzoyl |
| tBu | tertbutyl | TET | tetrazol-5-yl |
| Pn | n-pentyl | | |

One embodiment of this invention is represented by the compounds of the Formula (I) wherein $R^5$ is $CO_2R^7$.

One class of this embodiment is represented by the compounds of the Formula (I) wherein:

$R^1$ is tetrazol-5-yl or $SO_2NHCOR^3$ or $NHSO_2CF_3$ $R^3$ is
 a) phenyl,
 b) substituted phenyl in which the substituent is F, Cl, Br, I or $C_1$-$C_4$ alkoxy,
 c) $C_1$-$C_8$ alkyl substituted with di-($C_1$-$C_4$-alkyl)amino or $NH_2$, or
 d) $C_3$-$C_7$-cycloalkyl;

$R^4$ is
 a) $C_2$-$C_6$ alkyl,
 b) substituted $C_2$-$C_6$ alkyl in which the substituent is: CHO, $CO_2C_1$-$C_4$alkyl, $CO_2H$, $OC_1$-$C_4$ alkyl, cyclohexyl, phenyl, $NHCO_2tBu$,
 c) benzyl,
 d) substituted benzyl in which the substituent on the phenyl group is: F, Cl, Br, I, OH, $OPO(OC_1$-$C_4alkyl)_2$, $OPO(Obenzyl)_2$, $OPO(OH)_2$, —$PO(OC_1$-$C_4alkyl)_2$, —$PO(Obenzyl)_2$, $OPO(OH)_2$, $NO_2$, $NH_2$, $N(C_1$-$C_4$ alkyl$)_2$, Obenzyl,
 e) $CH_2$heteroaryl or
 f) $C_3$-$C_6$alkenyl;

$R^6$ is
 a) $C_1$-$C_6$ alkyl,
 b) substituted $C_1$-$C_6$ alkyl in which the substituent is: -benzyl, —$C_1$-$C_3$ alkyl, or —$OC_1$-$C_4$alkyl, or
 c) cyclopropyl;

$R^7$ is
 a) $C_1$-$C_6$ alkyl,
 b) benzyl,
 c) $C_2$-$C_4$alkyl-O—$C_1$-$C_4$alkyl or
 d) phenyl;

$R^{11}$ and $R^{12}$ are hydrogen,

Illustrating the first class of this embodiment are the following compounds (with their Example Number designation) of the Formula (I):

Exemplifications

| Example # | $R^6$ | $R^1$ | $R^7$ | $R^4$ |
|---|---|---|---|---|
| 1 | Pr | TET | iBu | Et |
| 3 | Bu | TET | iBu | Bn |
| 4 | Bu | TET | tBu | Me |
| 5 | Pr | TET | iBu | Bu |
| 6 | Pr | TET | Et | Me |
| 7 | Pr | TET | iPr | Me |
| 8 | Pr | TET | Me | Me |
| 9 | Pr | TET | Bu | Me |
| 10 | Pr | TET | iBu | Pr |
| 11 | Pr | TET | iBu | allyl |
| 12 | Pr | TET | iBu | Pn |
| 13 | Pr | TET | iBu | Pn |
| 14 | Pr | TET | iBu | (CH$_2$)$_3$Ph |
| 15 | Pr | TET | Me | Bn |
| 16 | Pr | TET | iBu | Bn |
| 17 | Pr | TET | Pr | Bn |
| 18 | Pr | TET | Bu | Bn |
| 19 | Pr | TET | Bn | Bz |
| 20 | Pr | TET | Hx | Bn |
| 21 | Pr | TET | tBu | Bn |
| 22 | Pr | TET | (CH$_2$)$_2$OMe | Bn |

-continued

Exemplifications

| Example # | $R^6$ | $R^1$ | $R^7$ | $R^4$ |
|---|---|---|---|---|
| 23 | Pr | TET | Pr | CH$_2$cHex |
| 24 | Pr | TET | Bu | Bu |
| 25 | Pr | TET | (CH$_2$)$_2$OEt | (CH$_2$)$_2$OMe |
| 47 | Et | TET | iBu | Me |
| 48 | Et | TET | iBu | Bn |
| 49 | iBu | TET | iBu | Me |
| 50 | iBu | TET | iBu | Bn |
| 51 | Me | TET | iBu | Bn |
| 52 | Me | TET | iBu | Me |
| 53 | Pr | SO$_2$NHCOPh | iBu | Me |
| 56 | Pr | TET | Et | Bn |
| 135 | Pr | TET | Ph | CH$_2$-2-Pyr |
| 150 | Et | TET | tBu | Bn |
| 151 | Et | TET | Bn | Bn |
| 152 | Bu | SO$_2$NHBz | iBu | Bn |
| 153 | Pr | SO$_2$NHCOcPr | Bu | Bn |
| 154 | Pr | SO$_2$NHBz | iBu | Bn |
| 155 | Pr | SO$_2$NHCOcPr | iBu | Me |
| 156 | Pr | TET | Pr | CH$_2$-4-Pyr |
| 157 | Pr | TET | (CH$_2$)$_2$OMe | Me |
| 158 | Pr | TET | Pr | CH$_2$-3-Pyr |
| 159 | Pr | TET | Pr | CH$_2$-2-Pyr |
| 160 | Pr | TET | (CH$_2$)$_2$OMe | CH$_2$-4-Pyr |
| 161 | CH$_2$OMe | TET | iBu | Me |
| 162 | CH$_2$OMe | TET | Pr | CH$_2$-2-Pyr |
| 163 | Pr | SO$_2$NHBz | Bn | Pn |
| 164 | Pr | TET | Et | CH$_2$-2-Pyr |
| 165 | Pr | TET | Pr | Bn-4-NO$_2$ |
| 166 | Pr | TET | Pr | Bn-4-NH$_2$ |
| 167 | Pr | TET | Pr | Bn-4-NMe$_2$ |
| 168 | H | TET | iBu | Me |

A second embodiment of this invention is represented by the compounds of the Formula (I) wherein $R^5$ is $CONR^8R^9$.

One class of this second embodiment is represented by the compounds of the Formula (I) wherein:

$R^1$ is tetrazol-5-yl or $SO_2NHCOR^3$ or $NHSO_2CF_3$ $R^3$ is
 a) phenyl,
 b) substituted phenyl in which the substituent is F, Cl, Br, I or $C_1$-$C_4$ alkoxy,
 c) $C_1$-$C_8$ alkyl substituted with di-($C_1$-$C_4$-alkyl)amino or $NH_2$, or
 d) $C_3$-$C_7$-cycloalkyl;

$R^4$ is
 a) $C_2$-$C_6$ alkyl,
 b) substituted $C_2$-$C_6$ alkyl in which the substituent is: CHO, $CO_2C_1$-$C_4$alkyl, $CO_2H$, $OC_1$-$C_4$ alkyl, cyclohexyl, phenyl, or $NHCO_2tBu$,
 c) benzyl,
 d) substituted benzyl in which the substituent on the phenyl group is: F, Cl, Br, I, OH, $OPO(OC_1$-$C_4alkyl)_2$, $OPO(Obenzyl)_2$, $OPO(OH)_2$, —$PO(OC_1$-$C_4alkyl)_2$, —$PO(Obenzyl)_2$, —$OPO(OH)_2$, $NO_2$, $NH_2$, $N(C_1$-$C_4$ alkyl$)_2$, or Obenzyl,
 e) $CH_2$heteroaryl, or
 f) $C_3$-$C_6$alkenyl;

$R^6$ is a) $C_1$-$C_6$ alkyl,
b) substituted $C_1$-$C_6$ alkyl in which the substituent is: -benzyl, —$C_1$-$C_3$ alkyl, or —$OC_1$-$C_4$alkyl, or
c) cyclopropyl;

$R^8$ is
a) $C_1$-$C_6$ alkyl or
b) hydrogen;

$R^9$ is
a) $C_1$-$C_6$ alkyl, or
b) when taken with $R^8$ and the nitrogen atom to which they are attached from a morpholinyl, N-($C_1$-$C_6$ alkyl)piperazinyl, N-($COC_1$-$C_6$ alkyl)-piperazinyl, or N-aryl-piperazinyl ring system.

$R^{11}$ and $R^{12}$ are hydrogen

Illustrating the first class of this second embodiment are the following compounds (with their Example Number designation) of the Formula (I):

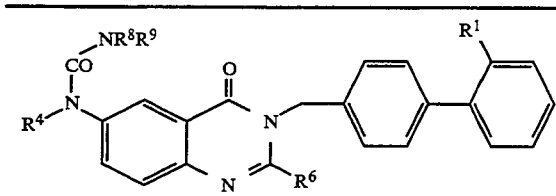

| Example # | $R^6$ | $R^1$ | $N(R^8)R^9$ | $R^4$ |
|---|---|---|---|---|
| 2 | Bu | TET | N(Me)iPr | Me |
| 31 | Pr | TET | N(Pn)$_2$ | Me |
| 29 | Pr | TET | N(Me)Pr | Bn |
| 30 | Pr | TET | N(Me)Et | Bn |
| 30 | Pr | TET | N(Me)Et | Bn |
| 40 | Pr | TET | morpholino | Bn |
| 173 | Et | TET | NHPr | Bn |
| 174 | Pr | TET | N(Me)iPr | Bn-4-F |
| 175 | Pr | TET | N(Me)iPr | CH$_2$-2-Pyr |

A third embodiment of this invention is represented by the compounds of the Formula (I) wherein $R^5$ is $COR^{10}$.

One class of this third embodiment is represented by the compounds of the Formula (I) wherein:

$R^1$ is tetrazol-5-yl, $SO_2NHCOR^3$ or $NHSO_2CF_3$;

$R^3$ is
a) phenyl,
b) substituted phenyl in which the substituent is F, Cl, Br, I or $C_1$-$C_4$ alkoxy,
c) $C_1$-$C_8$ alkyl substituted with di-($C_1$-$C_4$ alkyl)amino or $NH_2$, or
d) $C_3$-$C_7$-cycloalkyl;

$R^4$ is
a) $C_2$-$C_6$ alkyl,
b) substituted $C_2$-$C_6$ alkyl in which the substituent is: CHO, $CO_2C_1$-$C_4$alkyl, $CO_2H$, $OC_1$-$C_4$ alkyl, cyclohexyl, phenyl, or $NHCO_2tBu$,
c) benzyl,
d) substituted benzyl in which the substituent on the phenyl group is: F, Cl, Br, I, OH, $OPO(OC_1$-$C_4$alkyl$)_2$, $OPO(Obenzyl)_2$, $OPO(OH)_2$, —$PO(OC_1$-$C_4$alkyl$)_2$, —$PO(Obenzyl)_2$, $OPO(OH)_2$, $NO_2$, $NH_2$, $N(C_1$-$C_4$ alkyl$)_2$, Obenzyl, $OC_1$-$C_4$alkyl, COOH, or $CO_2CH_3$,
e) $CH_2$heteroaryl or
f) $C_3$-$C_6$alkenyl;

$R^6$ is
a) $C_1$-$C_6$ alkyl,
b) substituted $C_1$-$C_6$ alkyl in which the substituent is: -benzyl, —$C_1$-$C_3$ alkyl, or —$OC_1$-$C_4$alkyl or
c) cyclopropyl;

$R^{10}$ is
(a) phenyl,
(b) substituted phenyl in which the substituent is F, Cl, Br, I, methoxy, methyl, $CF_3$, SMe, $SO_2Me$, OH, $OPO(O$—$C_1$-$C_4$ alkyl $)_2$, $OPO(OH)_2$, OPO-$(OBn)_2$, $CO_2$-$C_1$-$C_4$alkyl, COOH, Obenzyl or $OC_6H_5$,
(c) benzyl,
(d) heteroaryl,
(e) $C_1$-$C_6$ alkyl or
(f) substituted $C_1$-$C_6$ alkyl substituted with: imidazole, piperazine, morpholinyl, N-($C_1$-$C_6$ alkyl) piperazinyl, N-($COC_1$-$C_6$ alkyl) piperazinyl, or N-aryl-piperazinyl;

$R^{11}$ and $R^{12}$ are hydrogen.

Illustrating the first class of this third embodiment are the following compounds (with their Example Number designation) of the Formula (I):

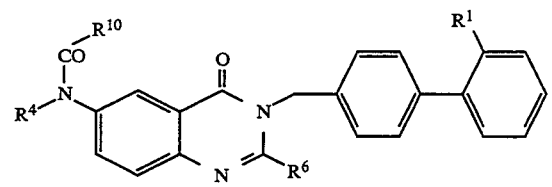

| Example # | $R^6$ | $R^1$ | $R^{10}$ | $R^4$ |
|---|---|---|---|---|
| 33 | Pr | TET | Ph | Pn |
| 34 | Pr | TET | Bn | Pn |
| 35 | Pr | TET | 4-Pyr | Pn |
| 36 | Pr | TET | Ph | Bn |
| 37 | Pr | TET | Ph-4-Cl | Pn |
| 37 | Pr | TET | Ph-4-Cl | Pn |
| 38 | Pr | TET | Ph-4-OMe | 4-methyl-pentyl |
| 39 | Pr | TET | 2-Furyl | Pn |
| 41 | Pr | TET | 3-methylbutyl | |
| 42 | Pr | TET | Bu | Bn |
| 43 | Pr | TET | Ph-4-F | Pn |
| 44 | Pr | TET | Ph-4-F | Bu |
| 45 | Pr | TET | Ph-4-Me | Pn |
| 46 | Pr | TET | Ph-3-Br | Pn |

-continued

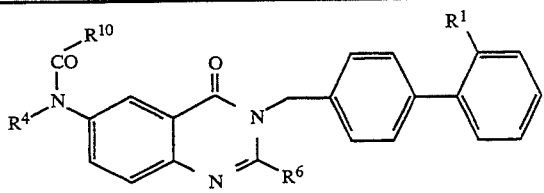

| Example # | R6 | R1 | R10 | R4 |
|---|---|---|---|---|
| 54 | Pr | TET | 3-Methylbutyl | Bn-4-OH |
| 55 | Pr | TET | Bu | Bu |
| 57 | Et | TET | Ph | Bn |
| 58 | Pr | TET | Ph-4-CF3 | Pn |
| 59 | Et | TET | Ph-4-F | Pn |
| 60 | 1-Methyl-pentyl | TET | Ph-4-F | Pn |
| 61 | Et | TET | PH-4-F | Bu |
| 62 | Et | TET | Ph | Bn-4-F |
| 63 | c-Pr | TET | Ph | Bn |
| 64 | c-Pr | TET | Ph | Pn |
| 65 | 1-Methyl-2-phenethyl | TET | Ph | Bn |
| 66 | c-Pr | TET | Ph | Bn |
| 67 | c-Pr | TET | Ph | Bn |
| 68 | Pr | TET | 4-Py | Bu |
| 69 | Me | TET | Ph | Bn |
| 70 | iPr | TET | Ph | Bn |
| 71 | Et | SO2NHBz | Ph | Bn |
| 72 | Pr | TET | 3-Pyr | Pn |
| 73 | Pr | SO2NHCOcPr | Ph | Pn |
| 74 | Pr | SO2NHBz | Ph | Pn |
| 75 | Et | TET | 4-Pyr | Bn |
| 77 | Pr | TET | Ph-4-SMe | Pn |
| 78 | Pr | TET | Ph | Pr |
| 79 | Et | TET | Ph-2-Cl | Bn |
| 80 | Et | TET | Ph-2-Cl | Bn-2-Cl |
| 81 | Pr | TET | Ph-4-SOMe | Pn |
| 82 | Pr | TET | Ph | (CH2)CHO |
| 83 | Pr | TET | Ph-4-SO2Me | Pn |
| 84 | Et | TET | Ph | Bn-2-Cl |
| 85 | Et | TET | Ph | CH2CH=CMe2 |
| 86 | Pr | SO2NHCOcPr | Me | Pr |
| 87 | Pr | SO2NHCOcPr | cPr | Pn |
| 88 | Pr | SO2NHCOcPr | Me | Pn |
| 89 | Pr | SO2NHCOPh | cPr | Pr |
| 90 | Pr | TET | Ph-4-F | Pr |
| 91 | Et | TET | Ph | iPn |
| 92 | iPr | TET | Ph | Bn-2-Cl |
| 93 | iPr | TET | cPr | Bn |
| 94 | iPr | TET | cPr | Bn-2-Cl |
| 95 | H | TET | Ph | Bn |
| 96 | H | TET | Ph | Bn-2-Cl |
| 97 | Et | TET | Ph | Bn-4-Cl |
| 98 | Et | TET | Ph | Bn-4-F |
| 99 | Et | TET | Ph | Bn-3-Et |
| 100 | 1-ethyl-ethyl | TET | Ph | Bn |
| 101 | 1-ethyl-ethyl | TET | Ph | Bn-2-Cl |
| 102 | Pr | TET | Ph | iBu |
| 103 | Pr | TET | Ph | (CH2)3CO2Et |
| 104 | Pr | NHSO2CF3 | Ph | Pn |
| 105 | Pr | TET | Ph | (CH2)3COOH |
| 106 | Me | TET | Ph | Bn-2-Cl |
| 107 | Me | TET | 4-Pyr | Bn |
| 108 | Pr | SO2NHCOcPr | Me | Me |
| 109 | Pr | TET | Ph | CH2CO2Et |
| 110 | Me | TET | 4-Pyr | Bn-2-Cl |
| 111 | Me | TET | 4-Pyr | CH2CH=CMe2 |
| 112 | Et | TET | Ph | Bn-4-I |
| 113 | Pr | TET | 2-thienyl | Pn |
| 114 | Pr | TET | 2-thienyl | Me |
| 115 | iPr | TET | Ph | Bn-4-I |
| 116 | Et | TET | Ph-4-I | Bn |
| 117 | Et | TET | Ph | Bz-2-I |
| 118 | Et | TET | 2-thienyl | Bn |
| 119 | Pr | TET | 4-Pyr | (CH2)2OMe |
| 120 | Pr | TET | Ph | CH2COOH |
| 121 | CH2OMe | TET | Ph-4-Cl | Pn |

-continued

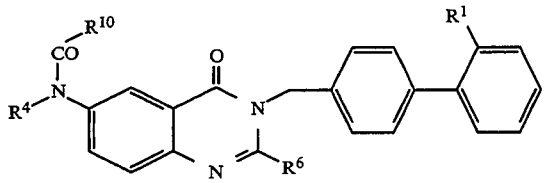

| Example # | R6 | R1 | R10 | R4 |
|---|---|---|---|---|
| 122 | Et | TET | 2-furoyl | Bn |
| 123 | Pr | TET | 2-thienyl | Bn |
| 124 | Pr | TET | 2-thienyl | Et |
| 125 | Pr | TET | 2-furoyl | Et |
| 126 | Pr | TET | Ph-2-OMe | Bn |
| 127 | Pr | TET | Ph-2-OMe | Pr |
| 128 | Pr | TET | Ph-4-OBn | Pn |
| 129 | Pr | TET | Ph-4-OBn | Pr |
| 130 | Pr | TET | Ph-4-OH | Pn |
| 131 | Pr | TET | Ph-4-OH | Pr |
| 132 | Pr | TET | CH2imidazole | Bn |
| 133 | Pr | TET | CH2PIPBoc | Bn |
| 134 | Pr | TET | 3-Pyr | Bn |
| 136 | Pr | TET | 2-Pyr | Bn |
| 137 | Pr | TET | Ph | CH2-2-Pyr |
| 138 | Pr | TET | Ph | CH2-4-Pyr |
| 139 | Pr | TET | 4-Pyr | Bn |
| 140 | Pr | TET | 2-Pyr | Bn |
| 141 | Me | TET | Ph | CH2-3-Pyr |
| 142 | Me | TET | Ph | CH2-2-Pyr |
| 143 | Pr | TET | Ph-4-OPO(OBn)2 | Pn |
| 144 | Pr | TET | Ph-4-OH | Bu |
| 145 | Pr | TET | 4-Pyr | CH2-2-Pyr |
| 146 | Pr | TET | Ph-4-OPO(OH)2 | Pn |
| 147 | Pr | TET | Ph-4-OH | Bn |
| 148 | Pr | TET | 2-furoyl | CH2-2-Pyr |
| 149 | Pr | TET | Ph-4-OPO(ONa)2 | Bu |

Note:
PIP — piperazinyl

A fourth embodiment of this invention is represented by the compounds of the Formula (I) wherein $R^5$ is $SO_2R^{10}$.

One class of this fourth embodiment is represented by the compounds of the Formula (I) wherein:
$R^1$ is tetrazol-5-yl, $SO_2NHSO_2CF_3$ or $NHSO_2CF_3$
$R^3$ is
 (a) phenyl,
 (b) substituted phenyl in which the substituent is F, Cl, Br, I or $C_1$–$C_4$ alkoxy,
 (c) $C_1$–$C_8$ alkyl substituted with di-($C_1$–$C_4$ alkyl)amino or $NH_2$, or
 (d) $C_3$–$C_7$-cycloalkyl;
$R^4$ is
 (a) $C_2$–$C_6$ alkyl,
 (b) substituted $C_2$–$C_6$ alkyl in which the substituent is: CHO, $CO_2C_1$–$C_4$alkyl, $CO_2H$, $OC_1$–$C_4$ alkyl, cyclohexyl, phenyl, or $NHCO_2tBu$,
 (c) benzyl,
 (d) substituted benzyl in which the substituent on the phenyl group is: F, Cl, Br, I, OH, OPO(OC1-C4alkyl)2, OPO(Obenzyl)2, OPO(OH)2, —PO(OC1-C4-alkyl)2, —PO(Obenzyl)2, —OPO(OH)2, NO2, NH2, N(C1-C4 alkyl)2, or Obenzyl,
 (e) CH2heteroaryl or
 (f) $C_3$–$C_6$alkenyl;
$R^6$ is
 (a) $C_1$–$C_6$ alkyl,
 (b) substituted $C_1$–$C_6$ alkyl in which the substituent is: -benzyl, —$C_1$–$C_3$ alkyl, or —$OC_1$–$C_4$alkyl or,
 (c) cyclopropyl;
$R^{10}$ is
 (a) phenyl,
 (b) substituted phenyl in which the substituent is F, Cl, Br, I, methoxy, methyl, $CF_3$, SMe, SOMe, $SO_2Me$, OH, OPO(O—$C_1$–$C_4$ alkyl)2, OPO(OH)2, OPO(OBn)2, $CO_2C_1$–$C_4$alkyl, or COOH,
 (c) benzyl,
 (d) heteroaryl,
 (e) $C_1$–$C_6$ alkyl, or
 (f) substituted $C_1$–$C_6$ alkyl substituted with: imidazole, piperazine, morpholinyl, N-($C_1$–$C_6$ alkyl)-piperazinyl, N-($COC_1$–$C_6$ alkyl)-piperazinyl, or N-aryl-piperazinyl;
$R^{11}$ and $R^{12}$ are hydrogen.

Illustrating this class of the fourth embodiment is the following compound (with its Example Number designation) of the Formula (I):

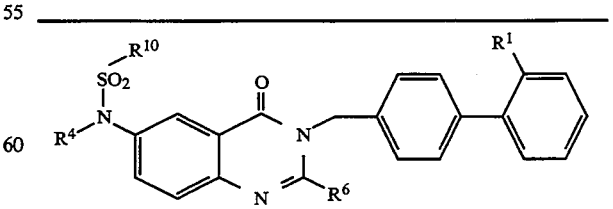

| Example # | R6 | R1 | R10 | R4 |
|---|---|---|---|---|
| 26 | Pr | TET | Bu | Bn |
| 169 | Et | TET | Pr | Pn |
| 170 | Et | TET | Bu | Pn |
| 171 | Et | TET | Pr | (CH2)3NHBoc |

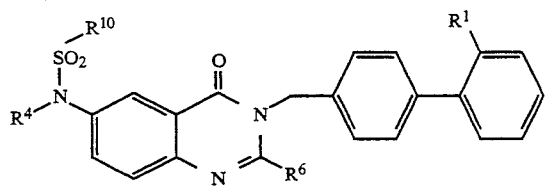

| Example # | $R^6$ | $R^1$ | $R^{10}$ | $R^4$ |
|---|---|---|---|---|
| 172 | Et | TET | Pr | Bn |

In naming compounds of Formula (I), it should be noted that the following two names for compound (i) shown below are considered to be equivalent:

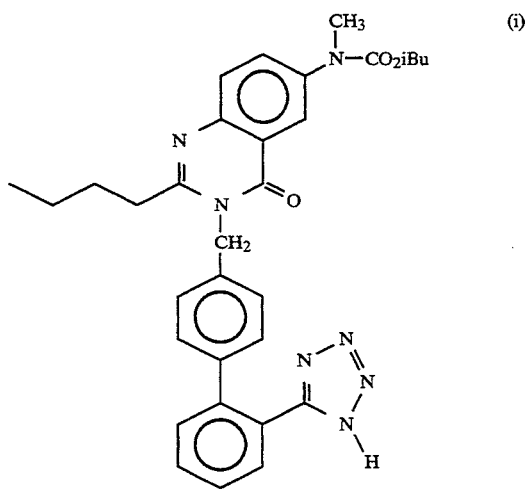

(1) 2-Butyl-6-(N-methyl-N-isobutyloxycarbonyl)-amino-3-[(2'-(tetrazol-5-yl)biphen-4-yl)methyl]quinazolin-4-(3H)-one; or, (2) 2-n-Butyl-6-(N-methyl-N-isobutyloxycarbonyl)-amino-3-[(2'-(tetrazol-5-yl)[1,1']-biphenyl-4-yl)methyl]-quinazolin-4(3H)-one.

| ABBREVIATIONS USED IN SCHEMES | |
|---|---|
| DNAP | Dimethylaminopyridine |
| -OTs | p-toluenesulphonate |
| -OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

Disubstituted 6-aminoquinazolin-4-(1H)-ones of the Formula (I) may be prepared from 2-cyano-4-nitroaniline (1) as described in Scheme 1. The 2-cyano-4-nitroaniline (1) is acylated using the requisite acyl chloride to give amide (2). The amide (2) is then cyclized with basic hydrogen peroxide to give the appropriately substituted 2-substituted 6-nitroquinazolin-4(3H)-one (3), which is then alkylated using sodium hydride and the appropriate alkyl halide (or pseudohalide)(9). The resulant 2,3-disubstituted 6-nitroquinazolin-4(3H)-one (4) is then reduced to the substituted 6-aminoquinazolin-4(3H)-one (5). The substituted 6-aminoquinazolin-4(3H)-one (5) is then transformed into the desired compounds of the Formula (I) utilizing standard chemical reactions as described below.

SCHEME 1

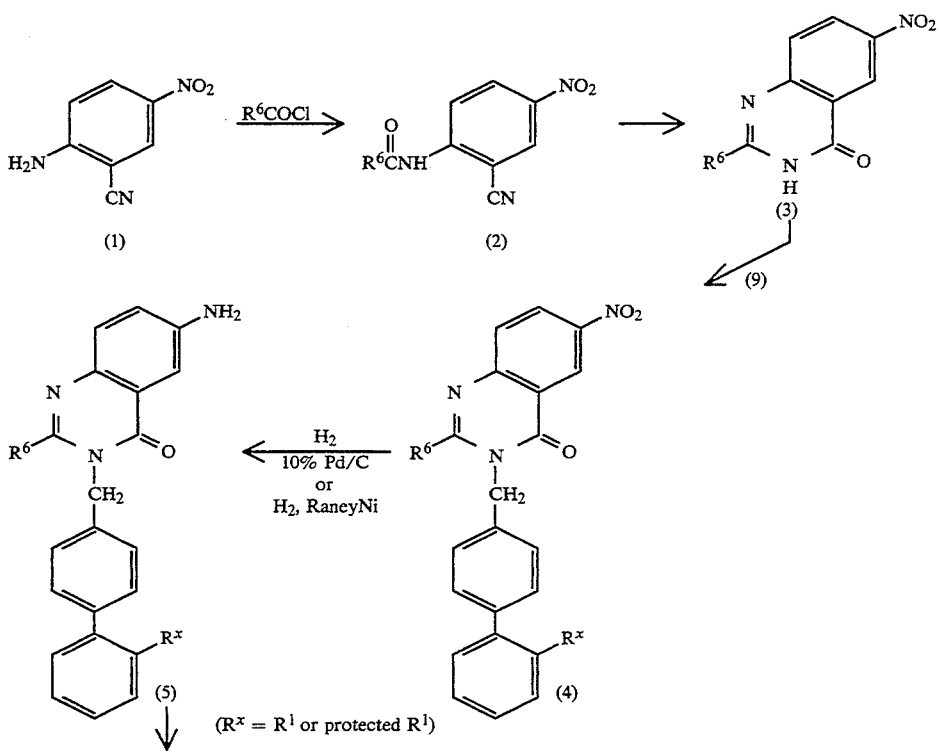

SCHEME 1
-continued

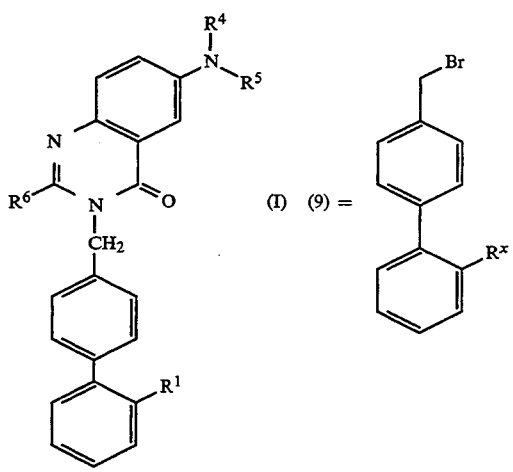

The benzyl halides (9) including the more preferred alkylating agents (9a and 9b, Scheme 2) can be prepared as described in European Patent Applications 253,310 and 291,969 and the references cited therein. However, a preferred method to prepare the biphenyl precursors (8a), (8b) and (8c) using Ni(O) or Pd(O) catalyzed cross-coupling reaction [E. Negishi, T. Takahashi, and A. O. King, Org. Synthesis, 66, 67 (1987)] is outlined in Scheme 2. As shown in Scheme 2, treatment of 4-bromotoluene (4a) with t-BuLi, followed by the addition of a solution of $ZnCl_2$, produces the organo-zinc compound (6a). Compound (6a) is then coupled with (7a) or (7b) in the presence of $Ni(PPh_3)_2Cl_2$ catalyst to produce the desired biphenyl compound (8a) or (8b) ($PPh_3$ = triphenylphosphine). Similarily, 1-iodo-2-nitrobenzene (7c) is coupled with organo-zinc compound (6a) in the presence of $Pd(PPh_3)_4$ catalyst [prepared by treating $Cl_2Pd(PPh_3)_2$ with $(i-Bu)_2AlH$ (2 equiv.)] to give the biphenyl compound (8c). These precursors, (8a), (8b) and (8c), are then transformed into halomethylbiphenyl derivatives (9a), (9b) and (9c), respectively, according to procedures described in European Patent Applications 253,310 and 291,969.

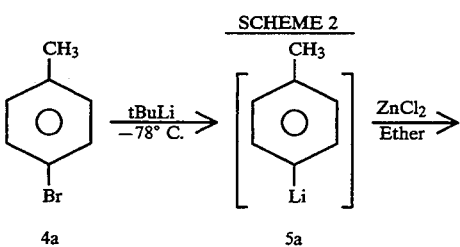

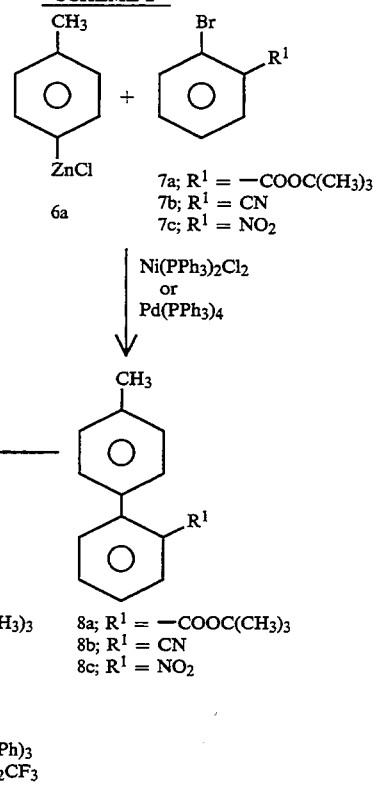

Scheme 3 shows an alternate preparation of 2-substituted 6-nitroquinazolin-4(3H)-ones (3) starting with the corresponding anthranilic acid. The appropriately substituted anthranilic acid (10) is treated with two equivalents of the requisite acyl chloride in DMF with triethylamine and DMAP at 0° C. This is then heated to 110° C. for two hours after which time excess ammonium carbonate is added. [M. T. Bogeft, W. F. Hand, J. Am. Chem. Soc. (1906) 28, 94.]

SCHEME 3

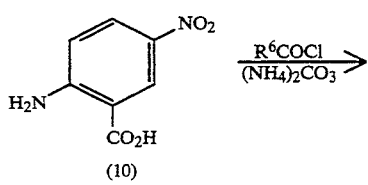

Schemes 4 and Scheme 5 provide an alternate route to compounds of Formula (I).

Two methods for preparing 1,3,4-benzoxazones (11) are illustrated in Scheme 4. Substituted anthranilic acids (10) may be acylated and cyclized by heating them in DMF with an acyl chloride, triethylamine and DMAP. [A. Khan, R. K. Saksena, *Pharmazie* (1988) 43 H. 12. L. A. Errede, J. J. McBrady, H. T. Oien, *J. Org. Chem.* (1977) 42, 656. L. A. Errede, *J. Org. Chem.* (1976) 41 1763. L. A. Errede, H. T. Oien, D. R. Yarian, *J. Org. Chem.* (1977) 42, 12. Alternatively, they may also be prepared by heating an appropriately substituted anthranil (12) with an acyl chloride in pyridine. K. Wunsch, A. J. Boulton, *Adv. Het. Chem.* (1967) 8, pp 326–9, and references therein. I. R. Gambhir, S. S. Joshi, *J. Ind. Chem. Soc.* (1964) 41, 47.

SCHEME 4

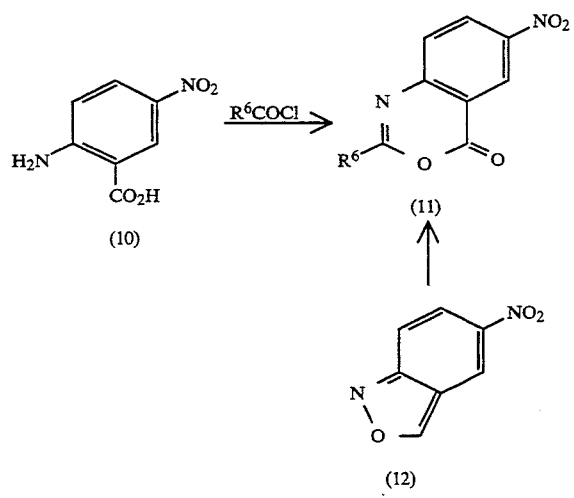

As shown in Scheme 5, the amine (13) and the 1,3,4-benzoxazone (11) are heated together to give the desired 2,3-disubstituted 6-nitroquinazolinone (4). The necessary alkyl amine (13) may be prepared from the alkyl halide (or pseudohalide) (9) using the standard literature procedures. Bayley, Stranding, Knowles, *Tetrahedron. Lett.* (1978) 3633. Rolla, *J. Org. Chem.* (1982) 47, 4327. Gibson, Bradshaw, *Angew, Chem, Int. Ed. Engl.* (1968) 7, 919.

SCHEME 5

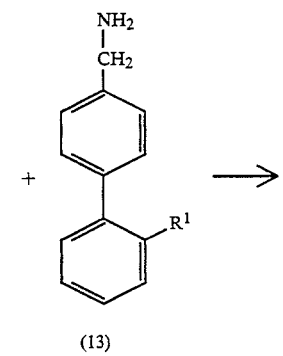

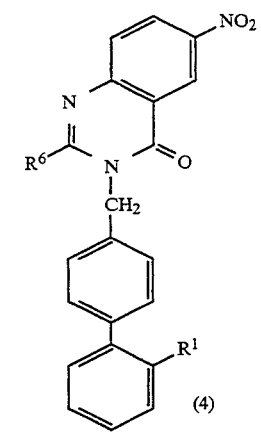

Functionalization of 2,3-disubstituted 6-nitroquinazolinone (4) is accomplished through the following synthetic pathways of Scheme 6, Scheme 7, Scheme 8, Scheme 9 and Scheme 10. The nitro group is reduced to the substituted 6-aminoquinazolin-(3H)-one (5) by reduction with hydrogen over palladium on carbon.

To prepare the compounds of the Formula (I) wherein $R^5$ is $CO_2R^7$, the chemical transformations in Scheme 6 are utilized. The acylation of the amine with chloroformates is best carried out in the presence of sodium hydride to form the anilinium anion. This anion reacts quickly with chloroformates to give the carbamates (14). The carbamate may be isolated and then deprotonated with lithium hexamethyldisilazide and alkylated to give the N,N-dialkylated carbamates (15). Alternatively this process may be carried out in one pot by first preforming the anilinium anion, acylating it and then deprotonating in situ and alkylating with $R^4$ iodide group to give (15). We have since found that 5 may be acylated with chloroformates under conventional conditions in the presence of $K_2CO_3$.

SCHEME 6

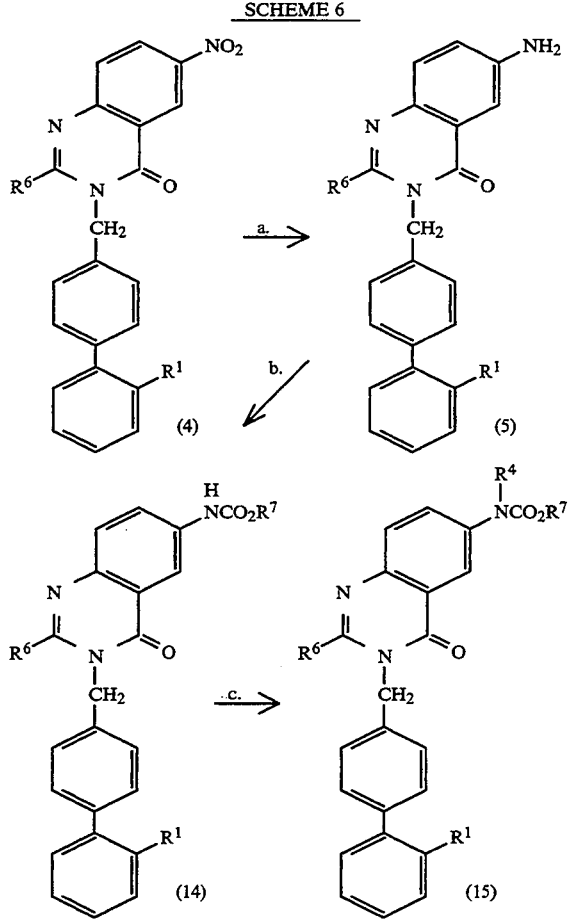

a. H₂, 10% Pd/C
b. NaH, R⁷CO₂Cl
c. LiN(TMS)₂, R⁴I

-continued
SCHEME 6

To prepare the compounds of the Formula (I) wherein $R^5$ is $CONR^8R^9$, the chemical transformations in Scheme 7 are utilized. The substituted 6-aminoquinazolin-4(1H)-one (5) reacts slowly with isocyanates to give ureas (16). Trisubstituted ureas (17) may be prepared from the benzyl carbamate (14) ($R^7$=benzyl) by treatment with the magnesium salt of a secondary amine ($HNR^8R^9$). The trisubstituted ureas may be N-alkylated by deprotonation with lithium hexamethyl-disilazide and alkylation with an $R^4$ iodide to give (18). The amine may be further derivatized or converted to other groups by means of chemical procedures well known to those skilled in the art.

SCHEME 7

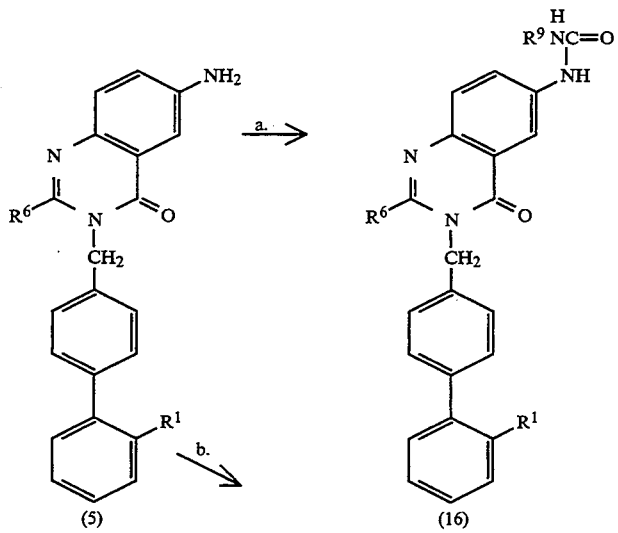

SCHEME 7

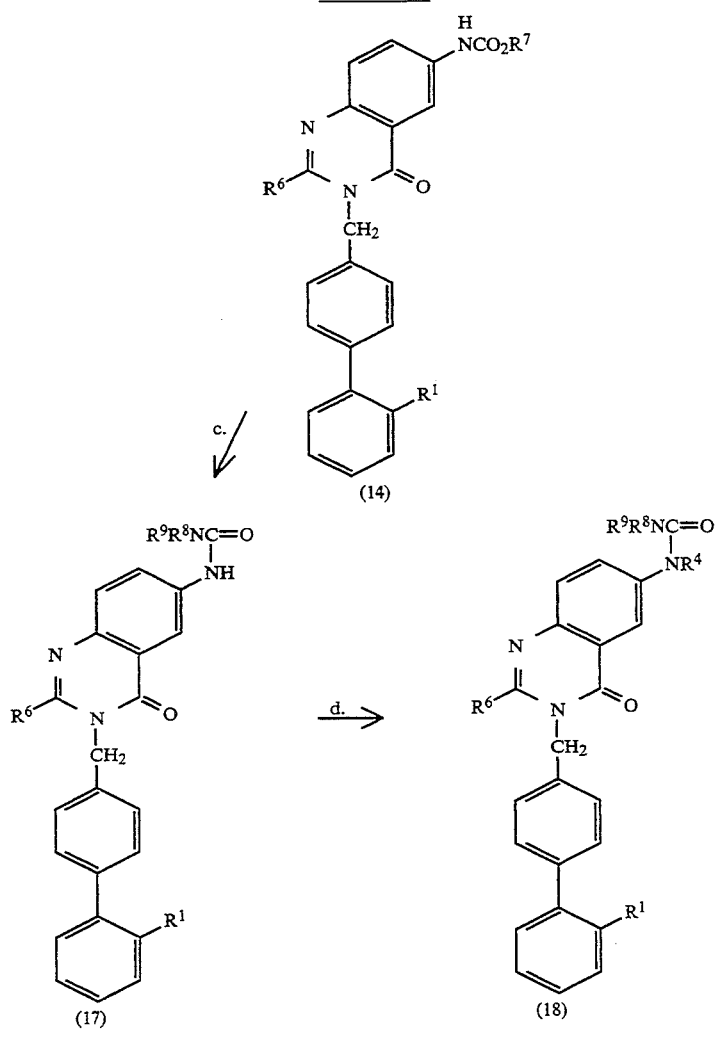

a. R⁹NCO
b. NaH, R⁷CO₂Cl
c. R⁸R⁹NMgBr
d. LiN(TMS)₂, R⁴I

To prepare the compounds of the Formula (I) wherein $R^5$ is $COR^{10}$, the chemical transformations in Scheme 8 are utilized. The substituted 6-amino-quinazolin-4(3H)-one (5) may then be acylated with acid chlorides to give amides (19) under basic conditions. The amide may be isolated and then deprotonated with lithium hexamethyldisilazide and alkylated to give (20). Alternatively, the amide may be alkylated with alkyl halide in the presence of potassium carbonate and sodium hydroxide and a phase transfer catalyst, such as tetrabutyl ammonium sulfate.

SCHEME 8

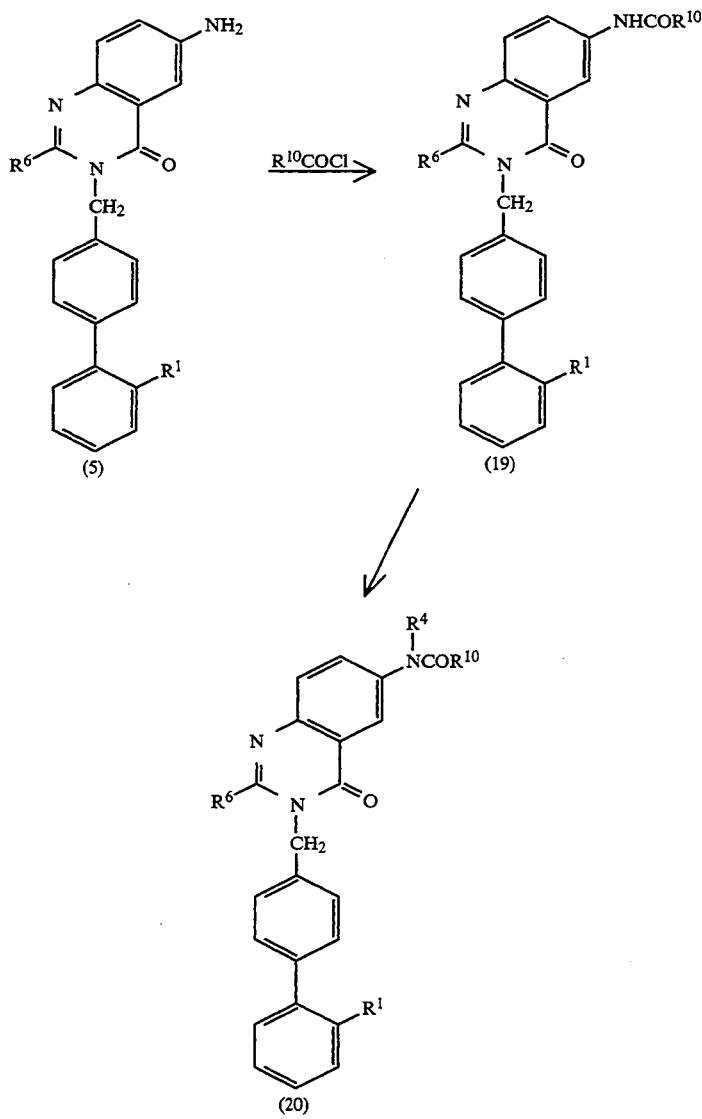

To prepare the compounds of the Formula (I) wherein $R^5$ is $SO_2NR^8R^9$, or $SO_2R^{10}$, the chemical transformations in Scheme 9 and Scheme 10 are utilized.

As shown in Scheme 9, the substituted 6-aminoquinazolin-4(1H)-one (5) may be sulfamylated with sulfamoyl chloride (21) to give sulfamide (22) which is then alkylated under basic conditions to yield the substituted sulfamide (23). Alternatively, the compound (5) may be N-monalkylated by a reductive alkylation or processed as the carbobenzyloxycarbonyl derivative and then alkylated as in Scheme 6 and then deprotected to give the N-monoalkyl derivative of compound (5). The N-monoalkyl derivative of compound (5) could then be sulfamylated with t-butyl sulfamoyl chloride, the t-butyl group could then be removed and the resultant amino group derivatized further to give the appropriately substituted sulfamide (23).

SCHEME 9

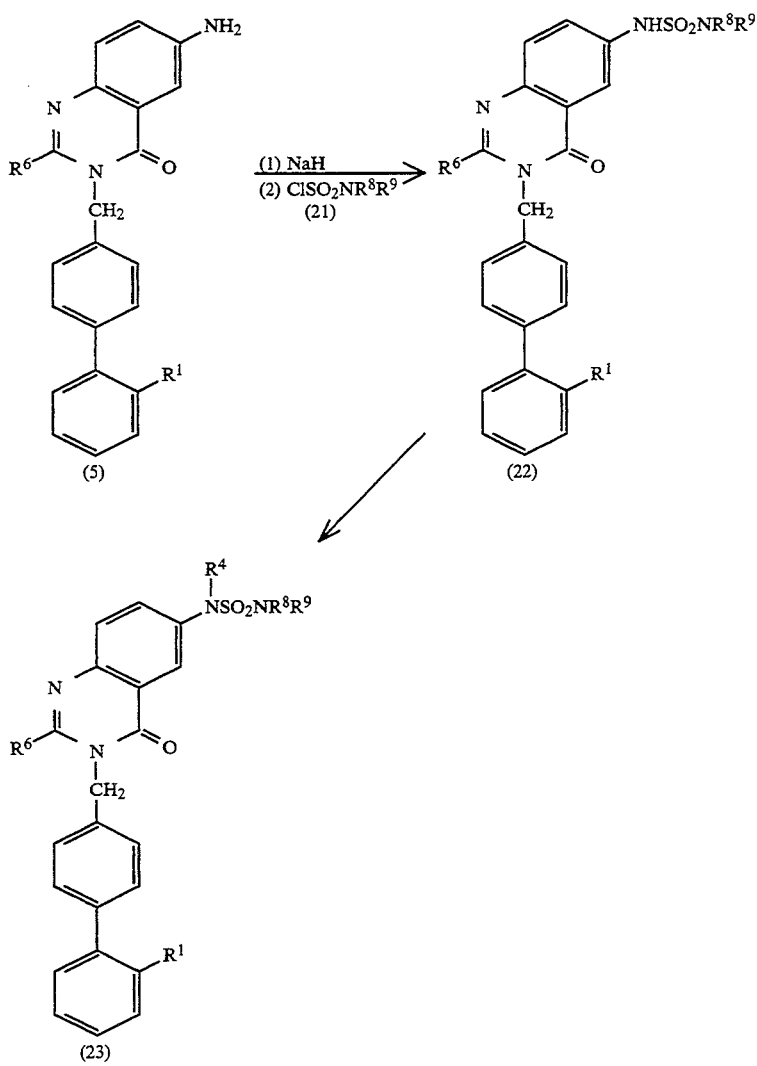

As shown in Scheme 10, the substituted-6-aminoquinazolin-4(1H)-one (5) is initially deprotonated with sodium hydride and then sulfonylated with an appropriate sulfonyl chloride. Alternatively, the compound (5) may be sulfonated in the presence of a tertiary amine. The sulfonamide may be isolated and puffled prior to alkylation or the crude sulfonamide prepared form the anilinium anion may be directly alkylated in situ. The alkylation may be carried out by deprotonating the sulfonamide and then adding an $R^4$ halide to yield the desired compounds (24)

SCHEME 10

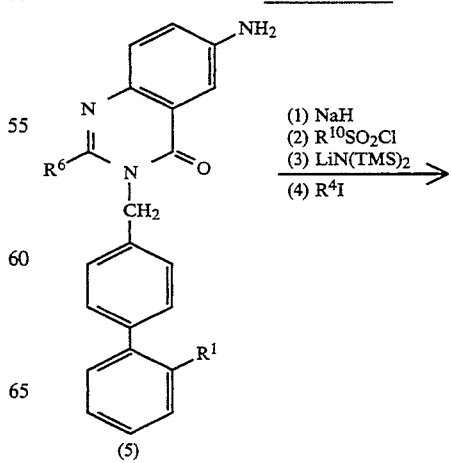

SCHEME 10 -continued

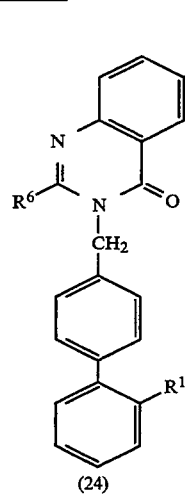

(24)

Compounds of formula (I) where R¹ is SO₂NHCOR³ may be prepared as outlined in Scheme 11. The nitro compound (8c) (prepared as described in Scheme 2) can be reduced to the corresponding amino compound and converted into aromatic diazoniun chloride salt, which then can be reacted with sulfur-dioxide in the presence of a copper (II) salt to form the corresponding arylsulfonyl chloride (26) [H. Meerwein, G. Dittmar, R. Gollner, K. Hafner, F. Mensch and O. Steifort, Chem. Ber., 90, 841 (1957); A. J. Prinsen and H. Cerfontain, Recueil, 84, 24 (1965); E. E. Gilbert, Synthesis, 3 (1969) and references cited therein]. The sulfonyl chloride can be reacted with ammonia in aqueous solution or in an inert organic solvent [F. H. Bergheim and W. Baker, J. Amer. Chem. Soc., 66, (1944), 1459], or with dry powdered ammonium carbonate, [E. H. Huntress and J. S. Autenrieth, J. Amer. Chem. Soc., 63 (1941), 346; E. H. Huntress and F. H. Carten, J. Amer. Chem. Soc., 62, (1940), 511] to form the sulfonamide (27). The benzylbromide (29) may be prepared from the sulfonamide (27) as outlined in Scheme 11, and then can be reacted with an alkali metal salt of an appropriate heterocyclic compound (30) to form the key sulfonamide (31). The sulfonamide (31) may be also prepared from the aromatic sulfonyl chloride (36), by treatment with ammonia, which may be prepared from the aryl amine (35) as outlined in Scheme 12. The acylation of (31) with appropriate acyl chlorides (or acyl-imidazoles or other acylating agents) may produce the desired acylsulfonamides (32). The sulfonamide 31 may then be acylated under appropriate conditions to give 32.

The compounds bearing R¹ as —SO₂NH-heteroaryl may be prepared by reacting the aromatic sulfonyl chloride (36) with appropriate heteroaryl amines as outlined in Scheme 12. The sulfonyl chloride (36) may be the preferred intermediate for the synthesis of this class of compounds. The aromatic sulfonyl chlorides may also be prepared by reacting the sodium salt of aromatic sulfonic acids with PCl₅ or POCl₃ [C. M. Suter, The Organic Chemistry of Sulfur, John Wiley & Sons, 459, (1944)]. The aromatic sulfonic acid precursors may be prepared by chlorosulfonation of the aromatic ring with chlorosulfonic acid [E. H. Huntress and F. H. Carten, J. Amer. Chem. Soc., 62, 511 (1940)].

SCHEME 11

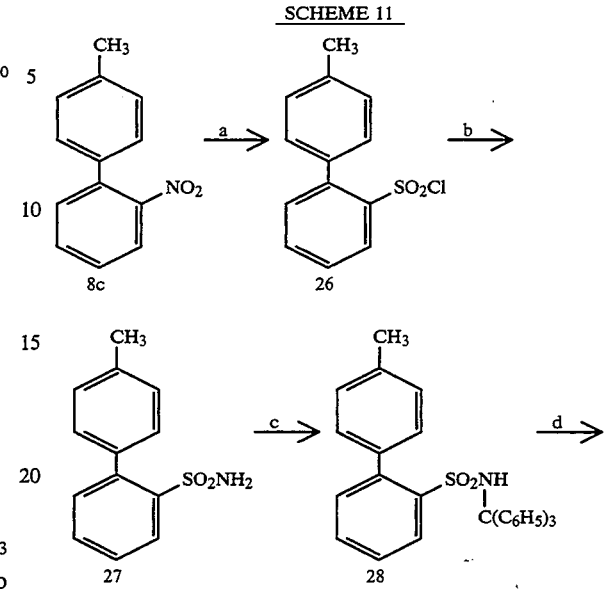

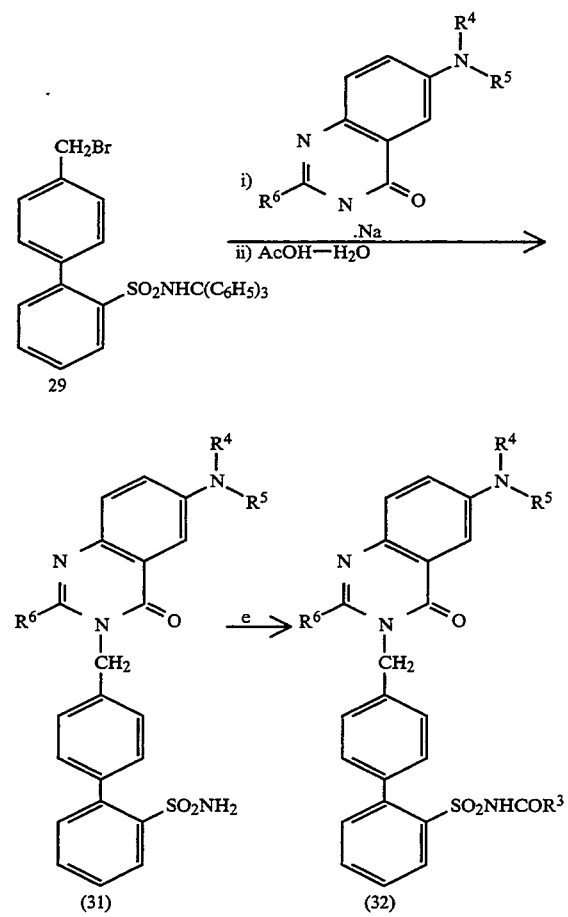

a. (i) H₂/Pd—C,
(ii) NaNO₂—HCl,
(iii) SO₂, AcOH, CuCl₂
b. NH₃ or (NH₄)₂CO₃
c. (C₆H₅)₃CCl, Et₃N, CH₂Cl₂, 25° C.
d. N-Bromosuccinimide
e. R³COCl or R³CO—Im or other acylating agents.

SCHEME 12
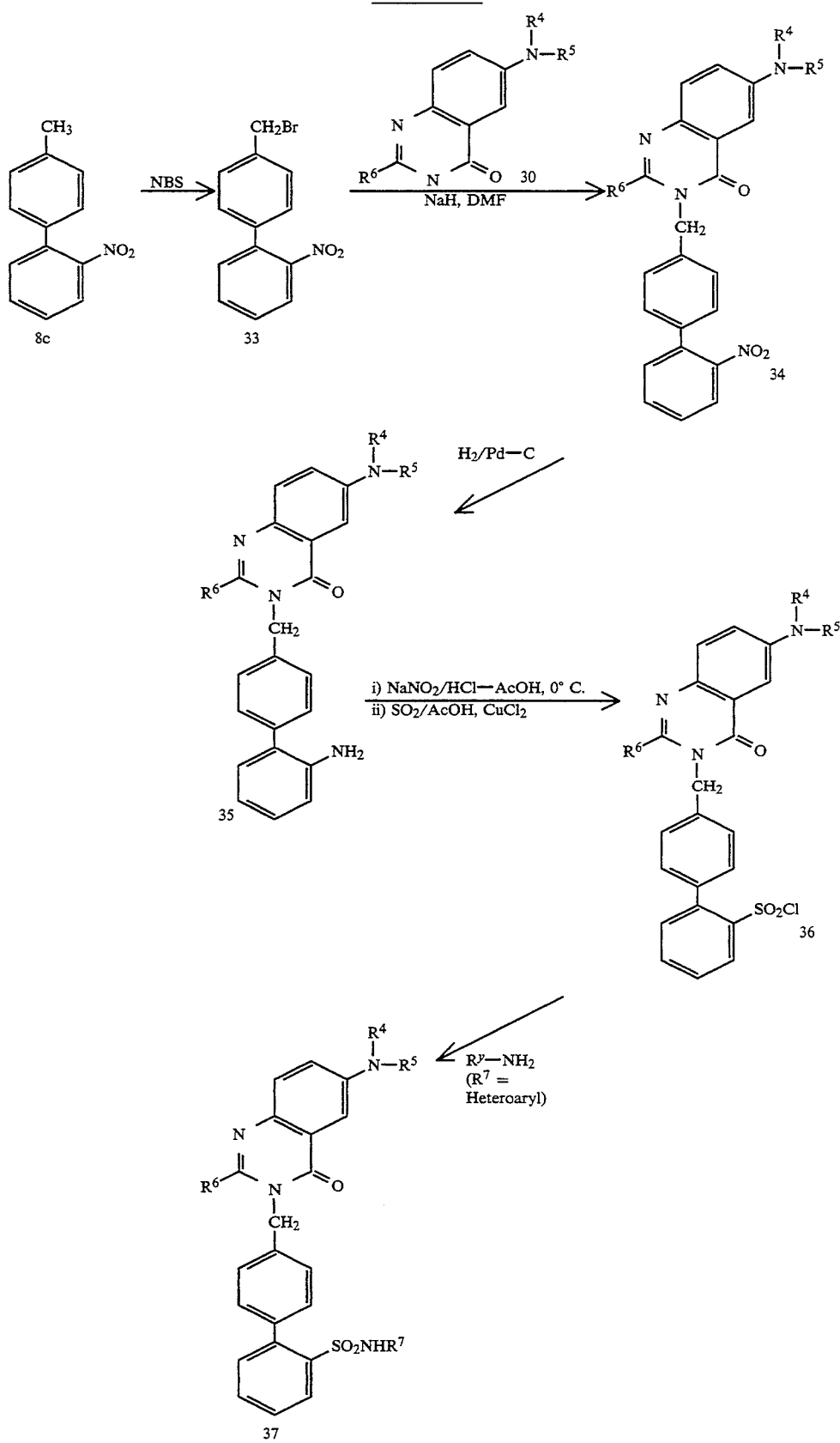
The 6-N-functionalized quinazolinones (30) may be prepared from the 6-nitroquinazolinones (3) as the dimethoxybenzhydryl derivative (33). Reduction of

(33) with 10% Pd/C and hydrogen gives amine (34) which is functionalized with R⁴ and R⁵ and described in prior Schemes to give (55). The dimethoxybenzhydryl group may be removed by treatment with acid to give (30).

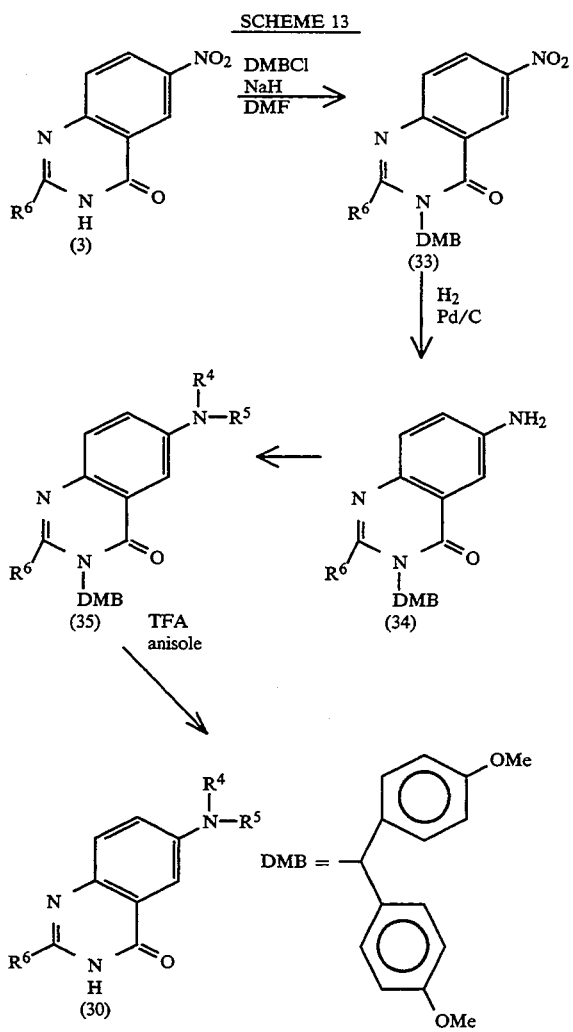

SCHEME 13

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight or MeOH/HCl is a preferred method to remove a trityl protecting group to liberate an $R^1$ tetrazole group.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar¹Ile⁸-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4″ diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar¹Ile⁸-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4″ diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 3H-angiotensin II was presented as a measure of the efficacy of such compounds as AII antagonists.

Receptor Assay Using Rat Brain Membrane Preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$,Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50$ mM thereby demonstrating and confirming the utility of the compounds of the invention as effective AII antagonists.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg),amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art-will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tactine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

In patients who are also hypertensive or have a congestlye heart failure condition, the compounds of this invention can be co-administered in combination with other antihypertensives and/or diuretics and/or angiotensin converting enzyme inhibitors and/or calcium channel blockers.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-400 Fourier transform spectrometer. Chemical shifts are reported as (parts per million) downfield from tetramethyl silane. Mass spectra were obtained from the Merck and Co. mass spectral facility in Rahway, N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of dry nitrogen under standard conditions for those skilled in the art.

The representative compounds of the Formula (I) as tabluated below have been prepared utilizing the following general and specific procedures.

PREPARATION OF QUINAZOLINONE HETEROCYCLES

6-nitro-2-propyl-quinazolin-4(1H)-one

To a suspension of 48.94 g (0.3 mol) of 3-nitro-5-amino-benzonitrile in 500 ml of $CH_2Cl_2$ was added 63 ml of $Et_3N$, 3 g DMAP and lastly, dropwise, 45.5 g (0.45 mol) of butyryl chloride. A mild exothermic reaction ensued. The mixture was allowed to stir for 2 days (monitor TLC with 50% EtOAc/hexanes). The solution was washed with 1N HCl (2×100 ml), water (1×100 ml) sat. $NaHCO_3$ (2×100 ml), brine (1×100 ml) and dried over $MgSO_4$. The suspension was filtered and concentrated in vacuo. The residue was suspended in a mixture of 600 ml of MeOH and 200 ml of water in a three neck round bottom flask. To this was added gradually 140 ml (0.7 m) of 5N NaOH solution followed by the dropwise addition of 80 ml of 30% $H_2O_2$ (0.7 mol) solution (beware of exothermic reaction!). The mixture was refluxed over night, cooled to room temperature and filtered. The filtrate was acidified with 1N HCl cooled to 5° C. and filtered. The quinazolinone may be recrystalized form hot MeOH to give 38 g of pale brown fine crystals. 54% yield. $^1$H-NMR-$CDCl_3$:1.10 (t, 3H, J=7.8 Hz), 1.93 (m, 2H), 2.79 (t, 2H, J=7.3 Hz), 7.81 (d, 1H, J=8.9 Hz), 8.55 (dd, 1H, J=2.4, 8.8 Hz), 9.14 (d, 1H, J=2.4 Hz), 10.72 (bs, 1H).

The following quinazolinones were prepared in the same manner as described above by using the appropriate acyl chloride:

2-n-Butyl-6-nitro-quinazolin-4(1H)-one $^1$H-NMR ($CDCl_3$): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

2-ethyl-6-nitro-quinazolin-4(3H)-one $^1$H-NMR ($CD_3OD$/$CDCl_3$-200 MHz): 1.35(t,3H. J=7.6 Hz), 2.70 (q, 2H, J=7.6 Hz), 7.74 (d, 1H ,. J=9.2 Hz), 8.48 (dd, 1H, J=9.2, J=2.8 Hz), 9.01(d, 1H, J=2.8 Hz).

2-methyl-6-nitro-quinazolin-4(3H)-one $^1$H-NMR (CDCl$_3$): 2.73 (s, 3H), 7.86 (d, 1H, J=9.0 Hz), 8.74 (dd, 1H, J=2.7, 9.0 Hz), 9.03 (d, 1H, J=2.7 Hz).

2-methoxymethyl-6-nitro-quinazolin-4(3H)-one

To a suspension of 13 g (0.08M) of 5-nitroanthranilonitrile in 100 ml of CH$_2$Cl$_2$ and 17 ml (0.12M) of triethyl amine and a catalytic quantity of DMAP was added 8.05 ml (0.88M) of methoxyacetyl chloride dropwise. The reaction was exothermic and was stirred over night at room temperature. The suspension was diluted with 100 ml of CH$_2$Cl$_2$ and washed with 1N HCl (3×30 ml), water (1×30 ml) and brine (1×50 ml) and the resulting solution was dried over MgSO$_4$, filtered and concentrated in vacuo to give 18.0 g of a yellow solid. To 10 g (0.042M) of this solid in 100 ml of MeOH was added 12.4 ml (0.062M) of 5M NaOH solution followed by the slow addition of 7.07 ml (0.062M) of 30% H$_2$O$_2$ in water. The reaction mixture was heated to reflux over night to give a suspension. The reaction mixture was filtered and the filtrate was acidified to give a yellow solid:2.57 g. 35% yield. 200 MHz-$^1$H-NMR (CDCl$_3$):3.58 (s, 3H), 4.52 (s, 2H), 7.46 (d, 1H, J=8.9 Hz), 8.54 (dd, 1H, J=2.6, 8.9 Hz), 9.14 (d, 1H, J=2.6 Hz), 9.90 (bs, 1H).

Preparation of 3-Alkylated Quinazolinones

6-Nitro-2-n-propyl-3-[(2'-(N-triphenylmethyl-tetrazol-5-yl)-biphen-4-yl)-methyl]-quinazolin-4(3H)-one To a suspension of 1.8 g (0.059 m) of 80% NaH in 150 ml of dry DMF at 0° C. under N$_2$ was added 12.64 g (0.054 m) of the 2-propyl-6-nitro quinazolinone as a solid portionwise. The resulting mixture gradually dissolved with evolution of H$_2$. To the resulting solution was added 40.7 g (0.059 m) of N-triphenylmethyl-5-[2-(4'-bromomethylbiphenyl)] tetrazole in 200 ml of dry DMF (10 min). The reaction mixture was allowed to warm to room temperature overnight. The TLC (50% EtAc/hexanes) indicates the formation of two products, a less polar O-alkylated product and more polar N-alkylated material. The reaction mixture was poured into 1300 ml of 0.1N NaOH (this removed any unreacted quinazolinone). The resulting yellow solid was recovered by filtration and then redissolved in CH$_2$Cl$_2$, washed with brine and dried over MgSO$_4$. The solution was filtered and concentrated in vacuo. The residue was purified by trituration with 50% EtOAc/hexanes. The unreacted bromide and O-alkylated products dissolve preferentially in the organic phase leaving the desired product as a solid. Recovered 32 g of a brown/grey solid.

2-n-Butyl-3-[(2'-(N-triphenylmethyl-tetrazol-5-yl)-biphen-4-yl)-methyl]-6-nitro quinazolin-4(3H)-one 2-n-Butyl-6-nitro-quinazolin-4(1H)-one was alkylated with N-triphenylmethyl-5-[2-(4'-bromomethylbiphenyl)] tetrazole in the same general manner as above. The product was purified by flash chromatography over silica gel eluting with 50% CH$_2$Cl$_2$/hexanes and gradually increasing the proportion of EtOAc to 15%. $^1$H-NMR (CDCl$_3$-300 MHz): 0.90 (t, 3H, J=7.5 Hz), 1.35 (m, 2H),1.72 (m, 2H), 2.72 (3 line m, 2H, 7.9 Hz), 5.31 (bs, 2H), 6.89–7.00 (m, 8H), 7.12 (d, 2H, J=8.0 Hz), 7.23–7.37 (m, 11H), 7.48 (m, 2H), 7.77 (d, 1H, J=9.0 Hz), 7.92 (m, 1H), 8.53 (dd, 1H, J=2.7,9.1 Hz), 9.18 9d, 1H, J=2.6 Hz).

2-ethyl-3-[(2'-(N-triphenylmethyl-tetrazol-5-yl)-biphen-4-yl)-methyl]-6-nitro quinazolin-4(3H)-one 2-ethyl-6-nitro-quinazolin-4(1H)-one was alkylated with N-triphenylmethyl-5-[2-(4'-bromomethylbiphenyl)] tetrazole in the same general manner as above. The product was purified by flash chromatography over silica gel. (CDCl$_3$-300 MHz): 1.28, (t, 3H, J=7.2 Hz), 2.72, (q, 2H, J=7.2 Hz), 5.32, (br.s, 2H), 6.89–7.01, (m, 8H), 7.13, (d, 2H, J=8.1 Hz), 7.21–7.38, (m, 10H), 7.45–7.55, (m, 2H), 7.81, (d, 1H, J=9.0, Hz), 7.98, (dd, 1H, J=8.0 Hz, J=2.4 Hz), 8.56, (dd, 1H, J=9.0 Hz,J=2.7 Hz), 9.21, (d, 1H, J=2.7 Hz).

2-methyl-3-[(2'-(N-triphenylmethyl-tetrazol-5-yl)-biphen-4-yl)-methyl]-6-nitro quinazolin-4(3H)-one 2-methyl-6-nitro-quinazolin-4(1H)-one was alkylated with N-triphenylmethyl-5-[2-(4'-bromomethylbiphenyl)] tetrazole in the same general manner as above. The product was purified by trituration with 10% EtOAc/hexanes to give a 60% yield of the title compound. (CDCl$_3$-300 MHz):

2-methoxymethyl-3-[(2'-(N-triphenylmethyl-tetrazol-5-yl)-biphen-4-yl)-methyl]-6-nitroquinazolin-4(3H)-one 2-methoxymethylquinazolin-4(3H)-one was alkylated in the same manner as described above for 6-nitro-2-n-propyl-3-[(2'-(N-triphenylmethyl-tetrazol-5-yl)-biphen-4-yl)-methyl]-quinazolin-4(3H)-one to give the title compound. 200 MHz-$^1$H-NMR (CDCl$_3$):3.43 (s, 3H), 4.36 (s, 2H), 5.46 (bs, 2H), 6.90 (m, 6H), 7.00 (d, 2H, J=8.2 Hz), 7.12 (d, 2H, J=8.2 H ), 7.19–7.38 (m, 10H), 7.48 (m, 2H), 7.84(d, 1H, J=8.9 Hz), 7.92 (m, 1H), 8.56 (dd, 1H, J=2.7, 9.01 Hz), 9.20 (d, 1H, J=2.6 Hz).

2-isopropyl-3-[(2'-(N-triphenylmethyl-tetrazol-5-yl)-biphen-4-yl)-methyl]-6-nitro quinazolin-4(3H)-one To the solution of 2-isopropyl-3-[(2'-(N-triphenylmethyl-tetrazol-5-yl)-biphen-4-yl)-methyl]-6-nitro quinazolin-4(3H)-one (85 mg, 0.12 mmol) in methylene chloride.(4 ml) were added (n-Bu)$_4$NBr (20 mg), methyl iodide(0.5 ml) and 50% aq. NaOH (1.0 ml) and the reaction mixture was stirred vigorously for 72 hrs at room temp. After diluting with water the organic layer was separated, evaporated in vacuo and the glassy residue was chromatographed on Chromatotron plate (hexane/AcOEt- 2/1) to furnish the title product as yellow glass. 200 MHz-$^1$H-NMR (CDCl$_3$): 1.24 (d, 6H, J=7.2 Hz), 3.08(sept.,1H,J=7.2 Hz), 5.36(m, 2H), 6.88–7.01(m, 8H), 7.12(d, 2H, J=8.0 Hz), 7.20–7.52(m, 12H), 7.77(d, 1H, J=8.8 Hz), 7.86–7.93(m, 2H), 8.52(dd,1H, J=8.8, J=2.6 Hz), 9.16(d, 1H,J=2.6 Hz).

Preparation of 6-Amino Quinazolinones

6-Amino-2-n-butyl-3-[(2'-(N-triphenylmethyl-tetrazol-5-yl)-biphen-4-yl)-methyl]-quinazolin-4(3H)-one A solution of 3.2 g (4.4 mmol) of 2-n-Butyl-3-[(2'-(N-triphenylmethyl-tetrazol-5-yl)-biphen-4-yl)-methyl]-6-nitro quinazolin-4(3H)-one in 100 mL of EtOAc was hydrogenated over night under atmospheric pressure in the presence of 0.5 g of 10% Pd/C. The solution was filtered through celite and the celite was washed with CH$_2$Cl$_2$ to remove any of the yellow coloured product. The filtrate was concentrated in vacuo to give 3.0 g of a pale yellow solid. The material was not purified further. 98% yield. $^1$H-NMR (CDCl$_3$-300 MHz): 0.89 (t, 3H, J=7.3 Hz), 1.32 (m, 2H), 1.69 (m, 2H), 2.62 (3 line m, 2H, J=7.9 Hz), 4.00 (bs, 2H), 5.29 (bs, 2H), 6.88–7.02 (m, 6H), 7.08–7.15 (m, 4H), 7.22–7.38 (m, 11H), 7.45–7.55 (m, 4H), 7.93 (dd, 1H, J=2.5, 7.0 Hz).

6-Amino-2-n-propyl-3-[(2'-(N-triphenylmethyl-tetrazol-5-yl)-biphen-4-yl)-methyl]-quinazolin-4(3H)-one 6-Nitro-2-n-propyl-3-[(2'-(N-triphenylmethyl-tetrazol-5-yl)-biphen-4-yl)-methyl]-quinazolin-4(3H)-one was hydrogenated as described above. The product was purified by flash chromatography over silica gel eluting with 7% acetone/CH$_2$Cl$_2$ to give a pale yellow solid. 72% yield. $^1$H-NMR (CDCl$_3$): 0.92 (m, 3H, J=7.7 Hz), 1.72 (m, 2H), 2.58 (3 line m, 2H, J=7.7 Hz), 5.56 (bs, 2H), 6.82–7.51 (m, 25H), 7.92 (dd, 1H, J-6.9, 1.9 Hz).

6-Amino-2-ethyl-3-[(2'-(N-triphenylmethyl-tetrazol-5-yl)-biphen-4-yl)-methyl]-quinazolin-4(3H)-one 6-Nitro-2-ethyl-3-[(2'-(N-triphenylmethyl-tetrazol-5-yl)-biphen-4-yl)-methyl]-quinazolin-4(3H)-one (0.11 g) was hydrogenated in dioxane (2.0 ml) sloution under 1 atm H$_2$ for 1 hr in the presence of Raney nickel catalyst.

6-Amino-2-methyl-3-[(2'-(N-triphenylmethyl-tetrazol-5-yl)-biphen-4-yl)-methyl]-quinazolin-4(3H)-one 6-Nitro-2-methyl-3-[(2'-(N-triphenylmethyl-tetrazol-5-yl)-biphen-4-yl)-methyl]-quinazolin-4(3H)-one was hydrogenated as described above. The product was purified by flash chromatography over silica gel eluting with 6% acetone/CH$_2$Cl$_2$ to give a pale yellow solid. 42% yield. $^1$H-NMR (CDCl$_3$-200 MHz): 2.34 (s, 3H), 3.95 (bs, 2H), 5.25 (bs, 2H), 6.82–7.53 (m, 17H), 7.95 (m, 1H).

6-Amino-2-methoxymethyl-3-[(2'-(N-triphenylmethyl-tetrazol-5-yl)-biphen-4-yl)-methyl]-quinazolin-4(3H)-one 2-methoxymethyl-3-[(2'-(N-triphenylmethyl-tetrazol-5-yl)-biphen-4-yl)-methyl]-6-nitroquinazolin-4(3H)-one was hydrogenated as described above. The product was purified by flash chromatography over silica gel eluting with 2% MeOH/CH$_2$Cl$_2$ to give a pale yellow solid. $^1$H-NMR (CDCl$_3$): 3.39 (s,3H), 3.71 (s, 2H), 4.30 (s, 2H), 5.55 (bs, 2H), 6.89–7.51 (m, 24H), 7.55 (d, 1H, J=14 Hz), 7.91 (m, 1H).

6-Amino-2-isopropyl-3-[(2'-(N-triphenylmethyl-tetrazol-5-yl)-biphen-4-yl)-methyl]-quinazolin-4(3H)-one 6-Nitro-2-isopropyl-3-[(2'-(N-triphenylmethyl-tetrazol-5-yl)-biphen-4-yl)-methyl]-quinazolin-4(3H)-one was hydrogenated overnight at 1 atm H$_2$ in dioxane solution in presence of Raney nickel catalyst as described above. The product was purified by flash chromatography over silica gel eluting with CH$_2$Cl$_2$/MeOH—20/1 to give a pale yellow solid. $^1$H-NMR (CDCl$_3$): 1.20, (d, 6H, J=6.4 Hz), 2.89–3.06, (m, 1H), 5.34, (br.s, 2H), 6.85–7.68, (m, 24H), 7.84–7.92, (m, 1H).

Preparation of
6-Amino-3-(4,4'-dimethoxybenzhydryl)-2-propyl-quinazolin-4(3H)-one Step 1

3-(4,4'-Dimethoxybenzhydryl)-2-propyl-6-nitro-quinazolin-4(3H)-one

To a suspension of 10.0 g (45 mmol) of 2-propyl-6-nitro-quinazolin-4(3H)-one in 160 ml of dry CH$_2$Cl$_2$ was added 9.5 ml (67 mmol) of triethylamine followed by 12.9 g (49 mmol) of 4,4'-dimethoxybenzhydryl chloride. The reaction mixture was stirred for 48 hours and then washed with 10% citric acid (2×20 ml), water (1×20 ml), saturated NaHCO$_3$ (2×20 ml) and brine (1×20 ml). The solution was dried over MgSO$_4$, filtered and concentrated in vacuo. The residue was recrystalised from EtOAc to give 17.3 g of white solid. 85% yield. $^1$H-NMR (CDCl$_3$): 0.87 (t, 3H, J=7.3 Hz), 1.58 (bm, 2H), 2.72 (t, 2H, J=7.8 Hz), 3.80 (s, 6H), 6.88 (d, 4H, J=9 Hz), 7.19 (d, 4H, J=9.0 Hz), 7.73 (d, 1H, J=8.9 Hz), 8.48 (dd, 1H, J=2.8, 9.0 Hz ), 9.08 (d, 1H, J=2.8 Hz).

Step 2

6-Amino-3-(4,4'-dimethoxybenzhydryl)-2-propyl-quinazolin-4(3H)-one

A solution of 12.1 g (26.0 mmol) of 3-(4,4'-dimethoxybenzhydryl)-2-propyl-6-nitro-quinazolin-4(3H)-one dissolved in 250 ml of EtOAc was hydrogenated under atmospheric pressure over three days in the presence of three portions of 1.2 g of 10% Pd/C. added daily. The mixture was filtered through celite and concentrated in vacuo to give an oil. The product was purified by flash chromatography over silica gel eluting with 50% EtOAc/hexanes to give 7.8 g (18.7 mmol) of the amine. 72% yield. $^1$H-NMR (CDCl$_3$):0.82 (t, 3H, J=7.2 Hz), 1.49 (bm, 2H), 2.61 (t, 2H, J=7.81 Hz), 3.79 (s, 6H), 3.90 (bs, 2H), 6.85 (d, 4H, J=8.8 Hz), 7.08 (dd, 1H, J=2.8, 8.7 Hz), 7.20 (d, 4H, J=8.4 Hz), 7.42 (d, 1H, J=2.7 Hz), 7.47 (d, 1H, J=8.7 Hz).

General Procedure for the Deprotection of the Tetrazole

The triphenyl methyl group was removed by dissolving for example, the C-6 derivatized quinazolinone (0.2 g) in MeOH (5 ml) in the presence of several drops (3–5) of concentrated hydrochloric acid. After 2 hours at room temperature a few crystals of phenopthalien were added and the reaction mixture was made basic by addition of 5N NaOH solution. The reaction mixture was reacidified by addition of acetic acid and then concentrated in vacuo. The residue was dissolved in 20 ml of EtOAc and washed with water (3×5 ml) and brine (1×5 ml) and dried over MgSO$_4$. The mixture was filtered and concentrated in vacuo and the residue was purified by flash chromatography over silica gel.

Alternatively, the triphenyl methyl group could be removed by stirring overnight in a solution of 3:1:1 acetic acid :water: THF, concentrating in vacuo and puriflying the residue with a suitable solvent mixture of suitalbe polarity (usually EtOAc/hexanes/1% acetic acid).

Described below are various general synthetic routes that were followed to prepare the compounds that are detailed in Table 1:

General Synthetic Routes to
6-Substituted Amino Compounds

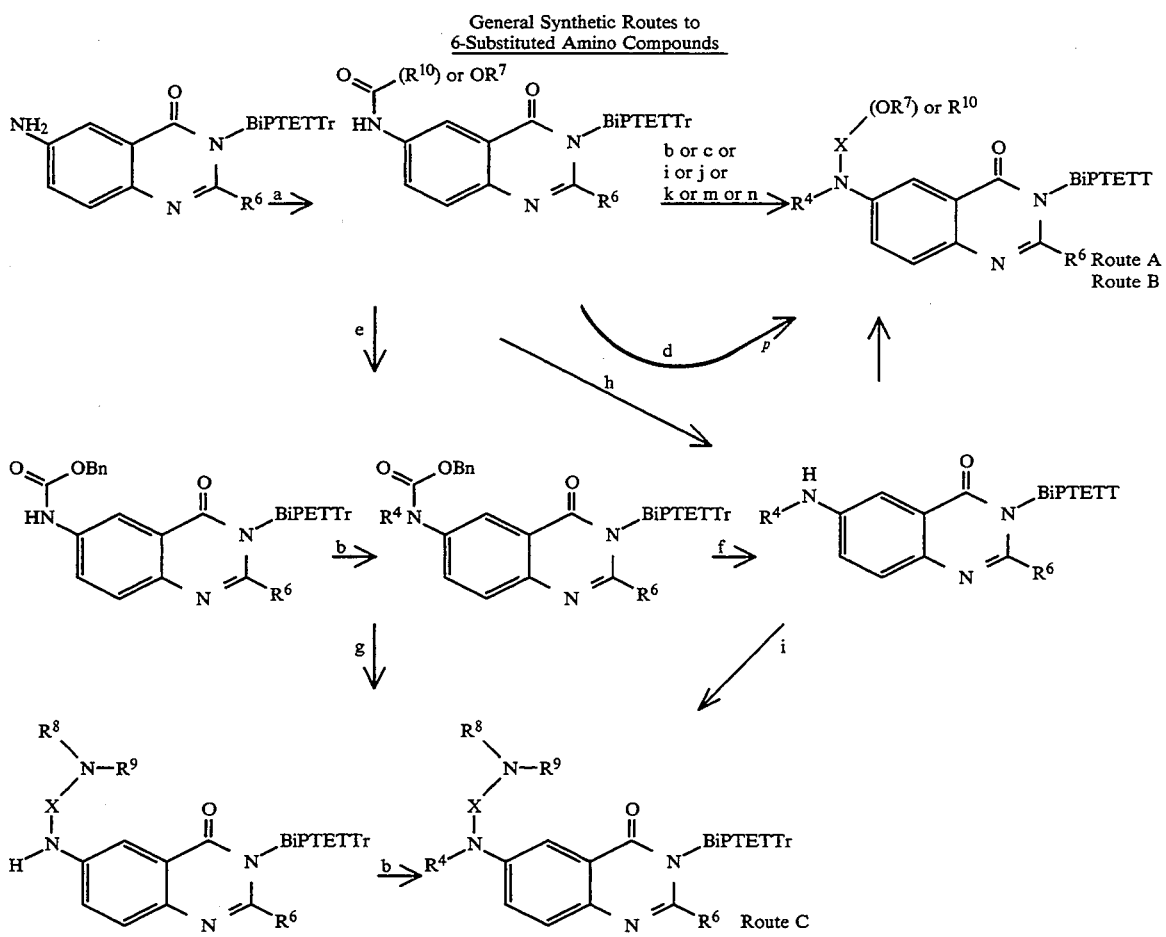

| ROUTE | STEP | TABLE OF REAGENTS: |
|---|---|---|
| A1 | d where X = $CO_2$ or $SO_2$ | a. $R^{10}COCl$ or $R^{10}SO_2Cl$, $Et_3N$ or $iPr_2NEt$, DMAP in $CH_2Cl_2$ |
| B1 | d where X = CO | b. $LiNTMS_2$, $R^4I$ or $R^4Br$ or $R^4Cl$, DMF. |
| B2a | a, b | c. $Bu^4NHSO_4$, toluene, $K_2CO_3$, $R^4I$ or $R^4Br$ or $R^4Cl$. |
| B2b | a, c. | d. NaH, $R^7OCOCl$ or $R^{10}COCl$ or $R^{10}SO_2Cl$ then $LiNTMS_2$, $R^4I$/DMF |
| B2d | a, j. | e. a with $R^{10}$ = OBn, X = CO |
| B2e | a, k. | f. $H_2$, 10% Pd/C. |
| B2f | a, m. | g. $R^8R^9NH$, MeMgBr, THF, 90° C. |
| B2g | a, n. | h. $R^4CHO$, toluene, heat then $NaBH_4$, in dioxane/$Et_2O$ |
| B2h | h, a. | i. NaH, DMF, $R^4$, or $R^4Br$ or $R^4Cl$. |
| B3 | e, b, f, a | j. t-BuOK, DMF, $R^4$, $R^4Br$ or $R^4Cl$ |
| C | e, g, b | k. $K_2CO_3$, DMF, $nBu_4NBr$, $R^4I$, $R^4Br$ or $R^4Cl$ |
| C2 | h, i | l. $R^8NCO$ heat |
| | | m. $nBu_4NBr$, $CH_2Cl_2$, NAOR 50%, $R^4I$, $R^4Br$ or $R^4Cl$ |
| | | n. $NaN(TMS)_2$, DMF, $R^4I$ or $R^4Br$ or $R^4Cl$. |

Experimental Directions for General Synthetic Routes to 6-Substituted Amino Compounds

ROUTE A1

Step d

To a suspension of 1.1 eq. of 80% NaH suspended in a volume of dry DMF that would make a 0.1M solution was added at 0° C. under $N_2$ a solution of 1.0 eq. of 6-amino-quinazolin-4(3H)-one dissolved in a minimal amount of DMF. After 30 min the chloroformate (ClCOOR$^7$) of choise was added neat. The reaction mixture was stirred for 30 minutes. To this mixture was added 1.2 eq of a 1M solution of lithium hexamethyldisilazide in THF. After 30 min. at 0° C. the alkylating agent ($R^4$) was added neat and the reaction mixture was stirred over night allowing the temperature to increase to room temperature. The reaction mixture was diluted with EtOAc (10 times the volume of DMF used) and washed with water (3×25% volume EtOAc used) and brine. The solution was dried over $MgSO_4$, filtered and concentrated in vacuo. The residue was purified by flash chromatography over silica gel eluting with a mixture of 20–50% EtOAc/hexanes to give the carbamate in 50–70% yield.

ROUTE B1

Step d

The method of Route A1 was followed acylating with an acid chloride (R[10]COCl) or R[10]SO$_2$Cl in place of the chloroformate R[7]CO$_2$Cl to give an amide.

ROUTE B2a

Step a

To a suspension of 0.48 mmol of 80% NaH in 2 ml of dry DMF was added at 0° C. under N$_2$ a solution of 0.44 mmol of 6-amino-2-alkyl-3-[(2'-(N-triphenylmethyl-tetrazol-5-yl)-biphen-4-yl)-methyl]-quinazolin-4(3H)-one in 1 ml of dry DMF. After 1 hour the acid chloride was added neat and the reaction mixture was stirred over night at room temperature. The reaction mixture was diluted with 50 ml of EtAc and washed with water (3×10 ml) and brine (1×10 ml) and dried over MgSO$_4$. The suspension was filtered and concentrated in vacuo and the residue was purified by flash chromatography over silica gel eluting with an appropriate mixture of EtOAc/hexanes. 50% yield.

Alternatively the amine can be acylated by following: To a solution of 1.4 mmol of 6-amino-2-alkyl-3-[(2'-(N-triphenylmethyl-tetrazol-5-yl)-biphen-4-yl)-methyl]-quinazolin-4(3H)-one in 5 ml of dry dichloroethane under N$_2$ was added 8.6 mmol of triethyl amine, 20 mg of dimethylaminopyridine and 2.1 mmol of the acyl or sulphonyl chloride. The reaction mixture was warmed to 60° C. over 48 hours, cooled and diluted with 100 ml of CH$_2$Cl$_2$ and washed with water (2×20 ml), brine (1×20 ml) and dried over MgSO$_4$. The reaction mixture was filtered and concentrated in vacuo and the residue was purified by flash chromatography over silica gel.

Alternatively the amine can be acylated by following: To a solution of 6-amino-2-alkyl-3-[(2'-(N-triphenylmethyl-tetrazol-5-yl)-biphen-4-yl)-methyl]-quinazolin-4(3H)-one.(0.49 mmol) in dioxane powdered K$_2$CO$_3$ (7.8 mmol) was added followed by acyl chloride (0.58 mmol). After 1 hr the reaction mixture was diluted with water and the product was extracted with AcOEt. Concentration in vacuo was followed by purification of the product on silica gel by radial chromatography.

Step b

To a solution of 0.4 mmol of the amide in 3 ml of dry DMF at 0° C. was added 0.44 mmol of a solution of lithium hexamethyl disilazide in hexanes. After 10 minutes the reaction mixture was treated with the alkylating reagent of choise and the reaction mixture was allowed to warm to room temperature over night. The solution was diluted with 25 ml of EtOAc and washed with water (3×5 ml) followed by brine and the organic phase was dried over MgSO$_4$, filtered and concentrated in vacuo. The residue was purified by either flash chromatography or by radial chromatography to give the compound of choise.

ROUTE B2b

Step a followed by Step c

To a solution of 0.4 mmol of the amide from route B2a 'step a' above in 3 ml of dry toluene was added 3.75 mmol of ground NaOH, 0.5 mmol of ground K$_2$CO$_3$ and 0.29 mmol of tetrabutyl ammonium sulfate. To this mixture was added 0.8 mmol of the alkylating agent of choice and the reaction mixture was heated to 60° C. over night. The mixture was diluted with 30 ml of EtOAc and washed with water (3×10 ml), brine (1×10 ml) and dried over MgSO$_4$. The mixture was filtered, concentrated in vacuo and the residue was purified by flash chromatography over silica gel eluting with mixtures of EtOAc/hexanes to give the amide of choice.

ROUTE B2c

Step a followed by Step i

To a flask containing NaH (0.12 mmol, washed with hexane) a solution of the secondary amide from route B2a step a above (0.06 mmol) in DMF (1 ml) was cannulated and stirred at room temp. for 0.5 hr. The alkylating agent (0.09 mmol) was added in one portion and after 1 hr the reaction was quenched with addition of water and extracted with ethyl acetate. The oily residue obtained after concentrating the organic layer in vacuo was purified by radial chromatography on silica gel eluting with hexane/ethyl acetate.-1/1.

ROUTE B2d

Step a followed by Step j

To a solution of the secondary amide from route B2a step a above (0.12 mmol) in dry DMF (2.0 ml) cooled to 0° C. t-BuOK (0.35 mmol) was added in one portion and after a few minutes alkylating agent was added. After overnight reaction at 0° C. the reaction mixture was diluted with water and extracted with CH$_2$Cl$_2$.and the tertiary amide of choise was purified by radial chromatography on silica gel eluting with hexane/ethyl acetate.-1/1.

ROUTE B2e

Step a followed by Step k

To a solution of the secondary sulphonamide from route B2a step a above (0.044 mmol) in DMF (0.5 ml) was added powdered K$_2$CO$_3$ (0.5 mmol), (n-Bu)$_4$NBr (0.1 equiv.) and alkylating agent (0.12 mmol). The reaction mixture was stirred vigorously for 24 hrs at room temperature, diluted with water and extracted with ethyl acetate. The tertiary sulfonamide of choise was purified by radial chromatography on silica gel eluting with hexane/ethyl acetate.-1/1.

ROUTE B2f

Step a followed by Step m

To a solution of the secondary amide from route B2a step a above (0.082 mmol) in CH$_2$Cl$_2$ (2.0 ml) were added alkylating agent (0.84 mmol), (n-Bu)$_4$NBr (0.1 equiv.) and 50% aq. NaOH solution. After vigorous stirring for 72 hrs the reaction mixture was diluted with water end extracted with CH$_2$Cl$_2$. The tertiary sulfonamide of choise was purified by radial chromatography on silica gel eluting with hexane/ethyl acetate.-1/1

ROUTE B2g

Step a followed by Step n

To a solution of the secondary amide from route B2a step a above (0.28 mmol) in DMF (2.0 ml) cooled to 0° C. was added sodium hexamethyldisilazide (1M in THF, 0.31 mmol) and after a few minutes the alkylating agent was added (in a small amount of DMF if solid). After stirring for 15 minutes at 0° C. the reaction mixture was diluted with water and extracted with ethyl acetate. The tertiary sulfonamide of choise was purified by radial chromatography on silica gel eluting with hexane/ethyl acetate.-1/1.

ROUTE B2h

Step h followed by step a Step h

The solution of 6-amino-2-alkyl-3-[(2'-(N-triphenylmethyl-tetrazol-5-yl)-biphen-4-yl)-methyl]-quinazolin- 4(3H)-one.(0.25 mmol) and appropriate benzaldehyde (2.5 mmol) in dioxane was refluxed under N₂ until no starting amine is present by TLC. The reaction mixture was diluted with ethanol (5 ml) and sodium borohydride (3.15 mmol) was added portionwise with occasional warming. After 2 hrs the reaction mixture was diluted with water and extracted with CH₂Cl₂. The benzylamine of choice was purified on Chromatotron plate with hexane/ethyl acetate elution.

ROUTE B3

Step e followed by Step b Step f

Hydrogenation as in the manner described above for the synthesis of 6-amino-2-n-butyl-3-[(2'-(N-triphenyl-methyl-tetrazol-5-yl)-biphen-4-yl)-methyl]-quinazolin-4(3H)-one. Step a.

ROUTE C

Step e followed by
Step g: (For example: The Preparation of Precursor to Example 2:)

To a solution of 0.1 g (0.12 mmol) of 2-n-Butyl-3-[(2'-(N-triphenylmethyl-tetrazol-5-yl)-biphen-4-yl)-methyl]-6-(N-carbobenzyloxy)-amino-quinazolin-4(3H)-one and 0.097 g (0.13 mmol) of isopropyl methyl amine in 3 ml of dry THF was added at 0° C. under N₂ 0.044 ml of a 3M solution of methyl magnesium bromide in THF. The solution was heated to 80° C. for 2 hours, cooled to room temperature, and treated cautiously with 10 ml of H₂O. The resulting mixture was extracted with EtOAc (3×10 ml). The combined organic extracts were washed with water (1×5 ml), brine (1×5 ml) and dried over MgSO₄ The mixture was filtered, concentrated in vacuo and purified by flash chromatography over silica gel eluting with 50% EtOAc/hexanes to give an oil. Followed by step b.

ROUTE C2

Step h followed by step l.

ROUTE D AND E

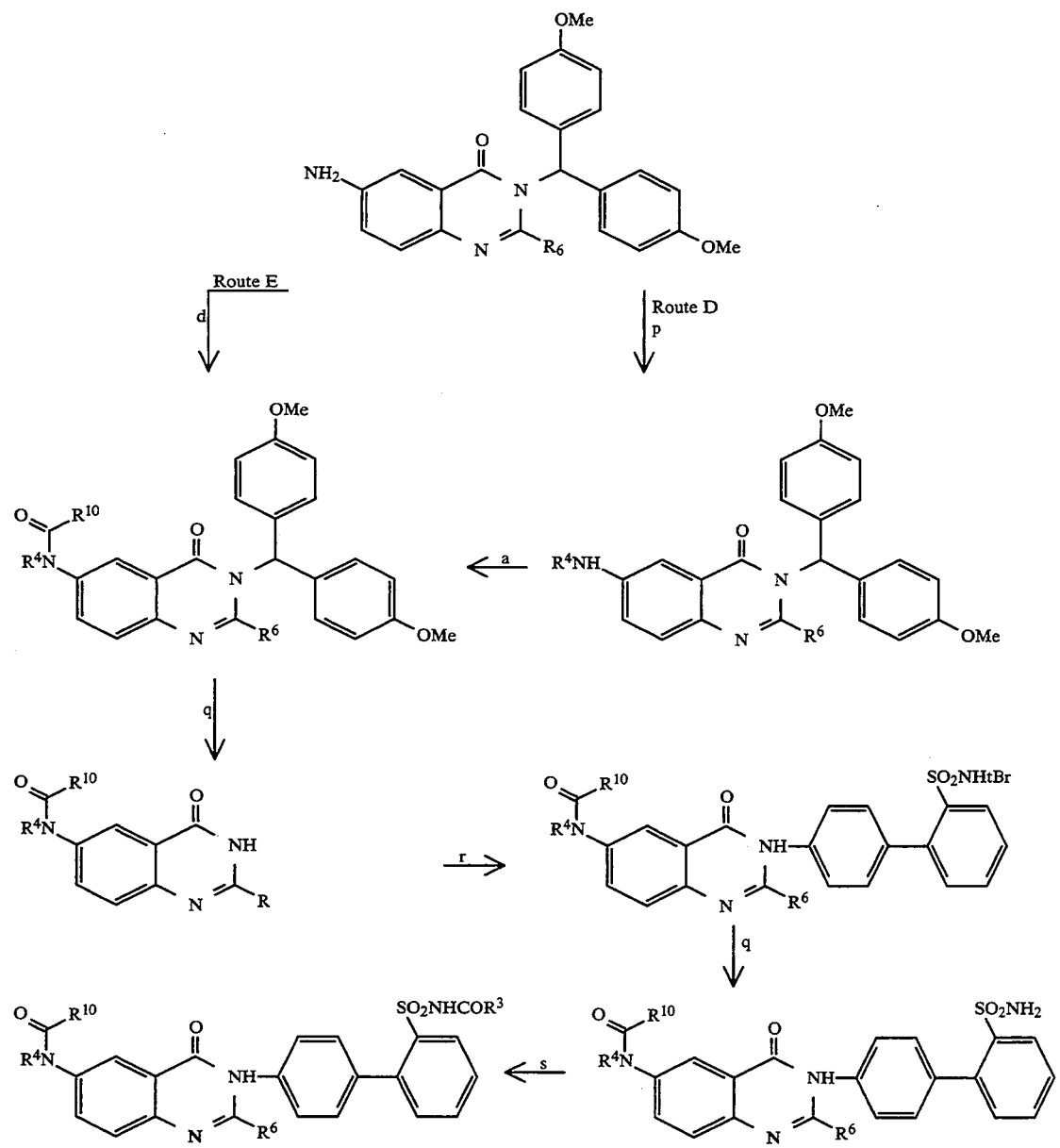

p.LiNTMS$_2$, R$^2$I, THF; q.TFA, Anisole; r. NaH, BrCH$_2$BIPSO$_2$NHtBu, DMF; S.R$^6$COOH, imCOim, DBU, THF, reflux

ROUTE D

1. Step p 3.0 g (6.99 mmol) of 6-Amino-3-(4,4'-dimethoxybenzhydryl)-2-propyl-quinazolin-4(3H)-one in 25 ml of dry THF at 0° C. was treated with 7.3 ml (7.3 mmol) of 1M lithium hexamethyl disilazide in hexanes. After 30 minutes (7.3 mmol) of the alkylating agent of choise was added and the reaction mixture was allowed to warm to room temperature over 3 hours and then stirred at room temperature over night. The reaction mixture was diluted with 200 ml of EtOAc, washed with water (3×50 ml) and brine (1×50 mL) and dried over MgSO$_4$, filtered and concentrated in vacuo. The residue was purified by flash chromatography over silica gel eluting with suitable mixture of EtOAc/hexanes to give the secondary amine of choise.

2. Step a 3. Step q

The dimethoxybenzhydryl protecting group was removed by dissolving the protected quinazolinone in 1 ml of 1:4 anisole:TFA per 100 mg of substrate. The reaction mixture was stirred over night at room temperature, concentrated in vacuo and the residue was purified by flash chromatography over silica gel eluting with a mixture of EtOAc/hexanes to give the deprotected quinazolinone.

4. Step r

The quinazolinone was alkylated with 4'-bromomethylbiphenyl-2-tert-butyl-sulfonamide in the general manner descibed for the preperation of starting materials.

5. Step q
6. Step s

General procedure for preparation of acyl sulfonamides: To a solution of 4 equivalents of carbonyl diimidazole in dry THF was added 4 equivalents of the carboxylic acid. The solution was heated to 50° C. for 2 hours under nitrogen. To this solution of acylimidazole was added 1 equivalent of the sulphonamide dissolved in THF with 4 equivalents of DBU. The solution was heated at 50° C. over night, diluted with EtOAc and washed with 10% citric acid, water and brine. The solution was dried over MgSO$_4$, filtered and concentrated in vacuo. The residue was purified by either flash chromatography or recrystalisation.

ROUTE E

1. Step d
2. Step q
3. Step r
4. Step q
5. Step s

ROUTE F

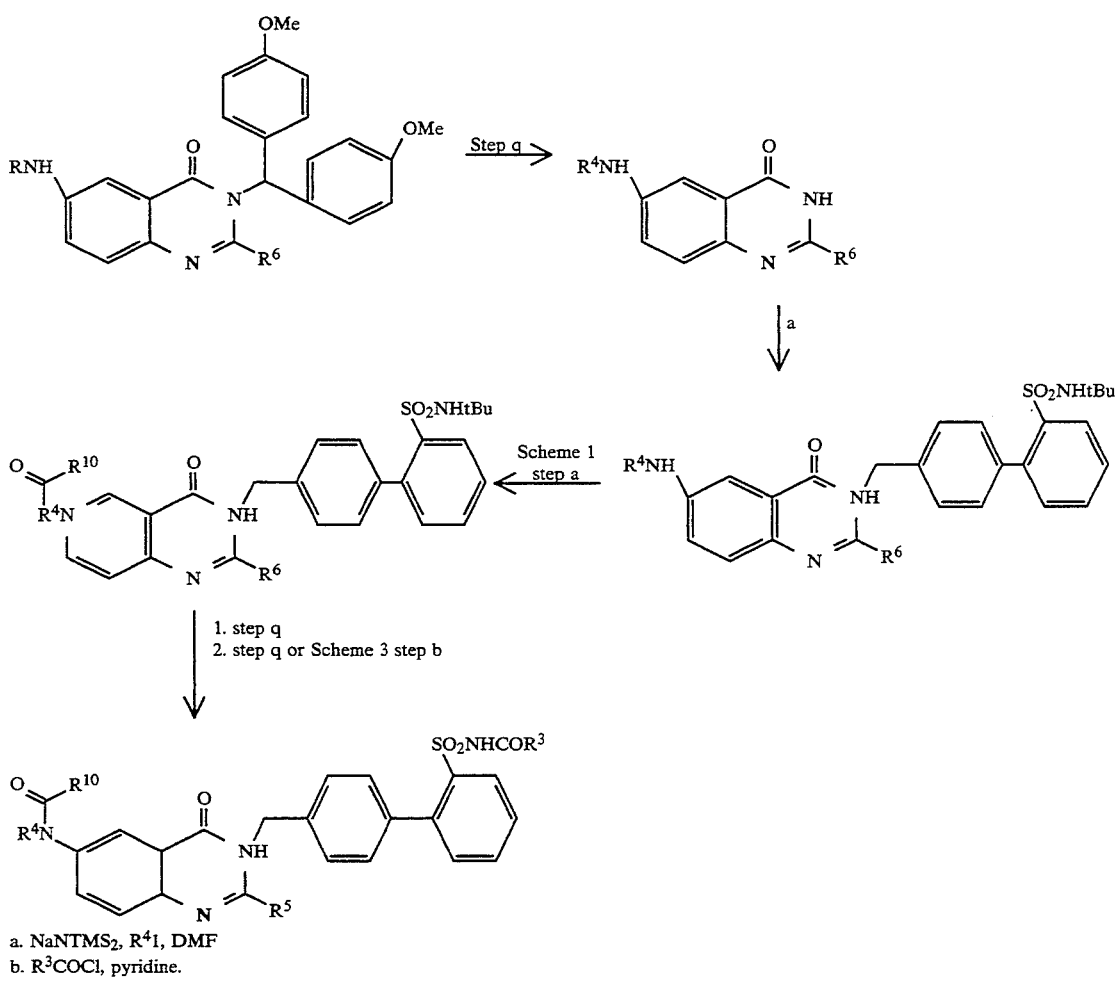

a. NaNTMS$_2$, R$^4$I, DMF
b. R$^3$COCl, pyridine.

ROUTE F

1. Scheme 2 step b
2. Step a

To a solution of the secondary amino quinazolinone in DMF at 0° C. was added was added 1.05 equivalents of sodium hexamethyl disilazide in THF followd after 10 minutes by a solution of 4'-bromomethylbiphenyl-2-tert-butyl-sulfonamide. The reaction mixture was stirred over night at room temperature and then diluted with EtOAc, washed with 10% citric acid, water and brine and was dried over MgSO4. The suspension was filtered and concentrated in vacuo and the residue was purified by flash chromatography over silica gel.

3. Scheme 1 step a

4. Scheme 2 step b then Scheme 2 step d or step b

The acyl sulfonamide may also be prepared by dissolution of the sulfonamide intermediate in pyridine and treatment with a five fold excess of an acyl chloride in the presence of DMAP. Following stirring over night the reaction mixture was concentrated in vacuo and the residue was dissolved in EtOAc and washed with 10% citric acid, water and brine and was dried over MgSO4. The suspension was filtered and concentrated in vacuo and the residue was purified by flash chromaotgraphy over silica gel.

Using the above general methods the compounds illustrated in Table 1 have been prepared, Below Table 1 is detailed the experimental and spectroscopic data for a representative sample of the Examples.

TABLE 1

| Ex # | $R^6$ | $R^1$ | $R^5$ | $R^4$ | Route | log P | MW |
|---|---|---|---|---|---|---|---|
| 1 | Pr | TET | COOiBu | Et | A1 | | 565 |
| 2 | Bu | TET | CON(Me)iPr | Me | C | | 564 |
| 3 | Bu | TET | COOiBu | Bn | A1 | | 641 |
| 4 | Bu | TET | COOtBu | Me | other | | 565 |
| 5 | Pr | TET | COOiBu | Bu | A1 | | 593 |
| 6 | Pr | TET | COOEt | Me | A1 | | 523 |
| 7 | Pr | TET | COOiPr | Me | A1 | | 537 |
| 8 | Pr | TET | COOMe | Me | A1 | | 509 |
| 9 | Pr | TET | COOBu | Me | A1 | | 551 |
| 10 | Pr | TET | COOiBu | Pr | A1 | 5.1 | 579 |
| 11 | Pr | TET | COOiBu | allyl | A1 | | 577 |
| 12 | Pr | TET | COOiBu | Pn | A1 | | 605 |
| 13 | Pr | TET | COOiBu | Pn | A1 | | 607 |
| 14 | Pr | TET | COOiBu | (CH2)3Ph | A1 | | 655 |
| 15 | Pr | TET | COOMe | Bn | A1 | | 585 |
| 16 | Pr | TET | COOiBu | Bn | A1 | | 627 |
| 17 | Pr | TET | COOPr | Bn | A1 | 5.0 | 613 |
| 18 | Pr | TET | COOBu | Bn | A1 | | 625 |
| 19 | Pr | TET | COOBn | Bz | A1 | | 661 |
| 20 | Pr | TET | COOHx | Bn | A1 | | 653 |
| 21 | Pr | TET | COOtBu | Bn | other | | 627 |
| 22 | Pr | TET | COO(CH2)2OMe | Bn | A1 | | 629 |
| 23 | Pr | TET | COOPr | CH2cHex | A1 | | 619 |
| 24 | Pr | TET | COOBu | Bu | A1 | 6.0 | 593 |
| 25 | Pr | TET | COO(CH2)2OEt | (CH2)2OMe | A1 | | 611 |
| 26 | Pr | TET | SO2Bu | Bn | A1 | | 647 |
| 29 | Pr | TET | CON(Me)Pr | Bn | C | | 626 |
| 30 | Pr | TET | CON(Me)Et | Bn | C | 4.3 | 612 |
| 31 | Pr | TET | CON(Pn)2 | Me | C | | 634 |
| 33 | Pr | TET | COPh | Pn | B1 | 5.1 | 649 |
| 34 | Pr | TET | COBn | Pn | B1 | | 625 |
| 35 | Pr | TET | CO4-Pyr | Pn | B2b | 4.3 | 612 |
| 36 | Pr | TET | COPh | Bn | B2a | 4.5 | 637 |
| 37 | Pr | TET | COPh-4-Cl | Pn | B1 | >6.0 | 646 |
| 37 | Pr | TET | COPh-4-Cl | Pn | B1 | >6.0 | 646 |
| 38 | Pr | TET | COPh-4-OMe | 3-methylbutyl | B2b | | 655 |
| 39 | Pr | TET | CO2-Furyl | Pn | B1 | | 611 |
| 40 | Pr | TET | COmorpholino | Bn | C | | 638 |
| 41 | Pr | TET | COiPn | BnOBn | B1 | | 731 |
| 42 | Pr | TET | COBu | Bn | B1 | 5.4 | 611 |
| 43 | Pr | TET | COPh-4-F | Pn | B2b | 5.2 | 629 |
| 44 | Pr | TET | COPh-4-F | Bu | B2b | 4.7 | 615 |
| 45 | Pr | TET | COPh-4-Me | Pn | B2b | | 625 |
| 46 | Pr | TET | COPh-3-Br | Pn | B2b | | 691 |
| 47 | Et | TET | COOiBu | Me | A1 | | 537 |
| 48 | Et | TET | COOiBu | Bn | A1 | | 613 |
| 49 | iBu | TET | COOiBu | Me | A1 | | 565 |
| 50 | iBu | TET | COOiBu | Bn | A1 | | 641 |
| 51 | Me | TET | COOiBu | Bn | A1 | | 598 |
| 52 | Me | TET | COOiBu | Me | A1 | | 522 |
| 53 | Pr | SO2NHCOPh | COOiBu | Me | E | | |
| 54 | Pr | TET | COiPn | Bn-4-OH | other | | 653 |

TABLE 1-continued

| Ex # | R6 | R1 | R5 | R4 | Route | log P | MW |
|---|---|---|---|---|---|---|---|
| 55 | Pr | TET | COBu | Bu | B1 | | 577 |
| 56 | Pr | TET | COOEt | Bn | A1 | 4.7 | 599 |
| 57 | Et | TET | COPh | Bn | B2h | 4.1 | 617 |
| 58 | Pr | TET | COPh-4-CF3 | Pn | B2b | | 680 |
| 59 | Et | TET | COPh-4-F | Pn | B2f | | 615 |
| 60 | 2-Me-Pn | TET | COPh-4-F | Bu | B2c | | 658 |
| 61 | Et | TET | COPh-4-F | Bu | B2d | | 601 |
| 62 | Et | TET | COPh | Bn-4-F | B2h | | 635 |
| 63 | c-Pr | TET | COPh | Bn | B2c | | 609 |
| 65 | 1-Me-2-Phenethyl | TET | COPh | Bn | B2f | | 707 |
| 66 | c-Pr | TET | COPh | Bn | B2c | | 629 |
| 68 | Pr | TET | CO4-Py | Bu | B3 | 4.1 | 597 |
| 69 | Me | TET | COPh | Bn | B2c | 3.5 | 603 |
| 70 | iPr | TET | COPh | Bn | B2c | 4.5 | 669 |
| 71 | Et | SO2NHBz | COPh | Bn | D | | 732 |
| 72 | Pr | TET | CO3-Pyr | Pn | B3 | 4.3 | 612 |
| 73 | Pr | SO2NHCOcPr | COPh | Pn | D | 5.3 | |
| 74 | Pr | SO2NHBz | COPh | Pn | D | 5.5 | 726 |
| 75 | Et | TET | CO4-Pyr | Bn | B2h | 3.4 | 618 |
| 76 | Et | TET | COPh | COPh | B2c | | 631 |
| 77 | Pr | TET | COPh-4-SMe | Pn | B2b | | 658 |
| 78 | Pr | TET | COPh | Pr | B2b | | 583 |
| 79 | Et | TET | COPh-2-Cl | Bn | B2c | | 652 |
| 80 | Et | TET | COPh-2-Cl | Bn-2-Cl | B2c | | 686 |
| 81 | Pr | TET | COPh-4-SOMe | Pn | other | 4.3 | 674 |
| 82 | Pr | TET | COPh | (CH2)CHO | other | | 598 |
| 83 | Pr | TET | COPh-4-SO2Me | Pn | other | 4.4 | 690 |
| 84 | Et | TET | COPh | Bn-2-Cl | B2c | 4.4 | 652 |
| 85 | Et | TET | COPh | CH2CH=CMe2 | B2c | 4.2 | 595 |
| 86 | Pr | SO2NHCOcPr | COMe | Pr | D | | 580 |
| 87 | Pr | SO2NHCOcPr | COcPr | Pn | D | | 654 |
| 88 | Pr | SO2NHCOcPr | COMe | Pn | D | | 608 |
| 89 | Pr | SO2NHCOPh | COcPr | Pr | D | | 662 |
| 90 | Pr | TET | COPh-4-F | Pr | B2b | 4.3 | 600 |
| 91 | Et | TET | COPh | iPn | B2c* | | 597 |
| 92 | iPr | TET | COPh | Bn-2-Cl | B2c | | 665 |
| 93 | iPr | TET | COcPr | Bn | B2c | | 595 |
| 94 | iPr | TET | COcPr | Bn-2-Cl | B2c | 4.8 | 629 |
| 95 | H | TET | COPh | Bn | B2c | 3.3 | 589 |
| 96 | H | TET | COPh | Bn-2-Cl | B2c | | 624 |
| 97 | Et | TET | COPh | Bn-4-Cl | B2c | | 652 |
| 98 | Et | TET | COPh | Bn-2-F | B2c | | 635 |
| 99 | Et | TET | COPh | Bn-3-Et | B2c | | 645 |
| 100 | 2-Me-Pr | TET | COPh | Bn | B2c | 4.9 | 646 |
| 101 | 2-Me-Pr | TET | COPh | Bn-2-Cl | B2c | | 680 |
| 102 | Pr | TET | COPh | iBu | B1 | 4.5 | 597 |
| 103 | Pr | TET | COPh | (CH2)3CO2Et | B2b | 4.1 | 655 |
| 104 | Pr | NHSO2CF3 | COPh | Pn | other | 5.7 | 658 |
| 105 | Pr | TET | COPh | (CH2)3COOH | other | 2.3 | 627 |
| 106 | Me | TET | COPh | Bn-2-Cl | B2g | 3.8 | 638 |
| 107 | Me | TET | CO-4-Pyr | Bn | B2c | 2.9 | 604 |
| 108 | Pr | SO2NHCOcPr | COMe | Me | D | 2.9 | 572 |
| 109 | Pr | TET | COPh | CH2CO2Et | B2b | | 627 |
| 110 | Me | TET | CO4-Pyr | Bn-2-Cl | B2g | 3.1 | 639 |
| 111 | Me | TET | CO4-Pyr | CH2CH=CMe2 | B2g | | 582 |
| 112 | Et | TET | COPh | Bn-4-I | B2g | 5.0 | 743 |
| 113 | Pr | TET | CO2-thienyl | Pn | B2b | 5.1 | 617 |
| 114 | Pr | TET | CO2-thienyl | Me | B2b | 3.4 | 561 |
| 115 | iPr | TET | COPh | Bn-4-I | B2g | | 757 |
| 116 | Et | TET | COPh-4-I | Bn | B2g | | 743 |
| 117 | Et | TET | COPh | Bz-2-I | B2g | 4.6 | 743 |
| 118 | Et | TET | CO2-thienyl | Bn | B2c | 4.1 | 623 |
| 119 | Pr | TET | CO4-Pyr | (CH2)2OMe | B3 | 3.0 | 601 |
| 120 | Pr | TET | COPh | CH2COOH | other | 2.1 | 599 |
| 121 | CH2OMe | TET | COPh-4-Cl | Pn | B2b | 4.6 | 648 |
| 122 | Et | TET | CO2-furoyl | Bn | B2h | 3.9 | 607 |
| 123 | Pr | TET | CO2-thienyl | Bn | B2c | | 637 |
| 124 | Pr | TET | CO2-thienyl | Et | B2b | 3.8 | 575 |
| 125 | Pr | TET | CO2-furoyl | Et | B2b | 3.5 | 559 |
| 126 | Pr | TET | COPh-2-OMe | Bn | B2b | 5.0 | 641 |

TABLE 1-continued

| Ex # | R⁶ | R¹ | R⁵ | R⁴ | Route | log P | MW |
|---|---|---|---|---|---|---|---|
| 127 | Pr | TET | COPh-2-OMe | Pr | B2b | 4.1 | 613 |
| 128 | Pr | TET | COPh-4-OBn | Pn | B2b | >5.7 | 717 |
| 129 | Pr | TET | COPh-4-OBn | Pr | B2b | 5.5 | 689 |
| 130 | Pr | TET | COPh-4-OH | Pn | other | 4.7 | 627 |
| 131 | Pr | TET | COPh-4-OH | Pr | other | 3.8 | 599 |
| 132 | Pr | TET | COCH₂Imidazole | Bn | other | 3.6 | 635 |
| 133 | Pr | TET | COCH₂PIPBoc | Bn | other | 5.3 | 753 |
| 134 | Pr | TET | CO3-Pyr | Bn | B3 | 3.7 | 618 |
| 135 | Pr | TET | COOPh | CH₂-2-Pyr | B2a | 3.6 | 632 |
| 136 | Pr | TET | CO2-Pyr | Bn | B3 | 3.8 | 632 |
| 137 | Pr | TET | COPh | CH₂-2-Pyr | B2a | 3.4 | 632 |
| 138 | Pr | TET | COPh | CH₂-4-Pyr | B2a | 3.4 | 632 |
| 139 | Pr | TET | CO4-Pyr | Bn | B1 | 3.7 | 632 |
| 140 | Pr | TET | CO2-Pyr | Bn | B3 | 3.7 | 632 |
| 141 | Me | TET | COPh | CH₂-3-Pyr | B1 |  | 604 |
| 142 | Me | TET | COPh | CH₂-2-Pyr | B2a |  | 604 |
| 143 | Pr | TET | COPh-4-OPO(OBn)₂ | Pn | other |  | 887 |
| 144 | Pr | TET | COPh-4-OH | Bu | other | 4.2 | 613 |
| 145 | Pr | TET | CO4-Pyr | CH₂-2-Pyr | B3 | 2.7 | 633 |
| 146 | Pr | TET | COPh-4-OPO(OH)₂ | Pn | other | 3.4 | 773 |
| 147 | Pr | TET | COPh-4-OH | Bn | other | 4.0 | 647 |
| 148 | Pr | TET | CO2-furoyl | CH₂-2-Pyr | B2 | 3.2 | 622 |
| 149 | Pr | TET | COPh-4-OPO(ONa)₂ | Bu | other |  | 759 |
| 150 | Et | TET | COOtBu | Bn | B2h |  | 613 |
| 151 | Et | TET | COOBn | Bn | B2h |  | 647 |
| 152 | Bu | SO₂NHBz | COOiBu | Bn | E |  | 756 |
| 153 | Pr | SO₂NHCOcPr | COOBu | Bn | E |  | 706 |
| 154 | Pr | SO₂NHBz | COOiBu | Bn | E |  | 742 |
| 155 | Pr | SO₂NHCOcPr | COOiBu | Me | E |  | 630 |
| 156 | Pr | TET | COOPr | CH₂-4-Pyr | A1 | 3.8 | 614 |
| 157 | Pr | TET | COO(CH2)2OMe | Me | A1 |  | 553 |
| 158 | Pr | TET | COOPr | CH₂-3-Pyr | A1 | 3.8 | 614 |
| 159 | Pr | TET | COOPr | CH₂-2-Pyr | A1 | 3.9 | 614 |
| 160 | Pr | TET | COO(CH₂)₂OMe | CH₂-4-Pyr | A1 | 2.7 | 630 |
| 161 | CH₂OMe | TET | COOiBu | Me | A1 | 3.7 | 553 |
| 162 | CH₂OMe | TET | COOPr | CH₂-2-Pyr | A1 | 3.3 | 616 |
| 163 | Pr | SO₂NHBz | COOBn | Pn | F |  | 756 |
| 164 | Pr | TET | COOEt | CH₂-2-Pyr | A1 | 3.5 | 600 |
| 165 | Pr | TET | COOPr | CH₂(-4-NO₂)Ph | A1 |  | 658 |
| 166 | Pr | TET | COOPr | CH₂(-4-NH₂)Ph | other | 3.9 | 628 |
| 167 | Pr | TET | COOPr | Bn-4-NMe₂ | other |  | 656 |
| 168 | H | TET | COOiBu | Me | A1 |  | 485 |
| 169 | Et | TET | SO2Pr | Pn | B2e |  | 599 |
| 170 | Et | TET | SO2Bu | Pn | B2e |  | 613 |
| 171 | Et | TET | SO2Pr | (CH₂)₃NHBoc | B2e |  | 686 |
| 172 | Et | TET | SO2Pr | Bn | B2h |  | 619 |
| 173 | Et | TET | CONHPr | Bn | C2 |  | 598 |
| 174 | Pr | TET | CON(Me)iPr | Bn-4-F | C | 4.8 | 644 |
| 175 | Pr | TET | CON(Me)iPr | CH₂-2-Pyr | C | 3.7 | 627 |
| 176 | Pr | TET | COPh-2-OEt | Bn | B2a |  | 675 |
| 177 | Pr | TET | COPh-4-OMe | Bn-4-OMe | B2a |  | 691 |
| 178 | Pr | TET | COPh-2-OPh | Bn | B2a | 4.2 | 723 |
| 179 | Pr | TET | COPh | Bn-4-OH | other | 3.6 | 647 |
| 180 | Pr | TET | COPh-4-COOH | Bn | other | 2.9 | 675 |
| 181 | Pr | TET | COPh-4-OH | CH₂-3-Pyr | as in 147 | 2.8 | 648 |
| 182 | Pr | TET | COPh | Bn-4-COOH | from 183 | 2.4 | 675 |
| 183 | Pr | TET | COPh | Bn-4-CO₂Me | B2a | 4.4 | 687 |

* = product of Pd/C hydrogenation of Example 85.

The conditions used for the purification and some representative NMR spectral data is given below for some of the compounds described above (The acid group is tetrazol-5-yl).

| Ex # | R6 | R | R5 | Chomatography Conditions | FABMS M⁺ + 1 |
|---|---|---|---|---|---|

-continued

| | | | | | |
|---|---|---|---|---|---|
| 3 | Bu | Bn | COOiBu | 50% EtOAC/hexanes 1% AcOH | 642 |
| 6 | Pr | Me | COOET | 50% EtAc/hexanes 1% AcOH | 524 |
| 7 | Pr | Me | COOi-Pr | 50% EtAc/hexanes 1% AcOH | 538 |
| 8 | Pr | Me | COOME | 70% EtAc/hexanes 1% AcOH | 510 |
| 9 | Pr | Me | COOnBu | 30% EtAc/hexanes 1% AcOH | 552 |
| 10 | Pr | Pr | COOi-Bu | 50% EtAc/hexanes 1% AcOH | 594 |
| 11 | Pr | Allyl | COOi-Bu | 50% EtoAc/hexanes 1% AcOH | 578 |
| 12 | Pr | 3-Methyl-butyl | COOi-Bu | 50% EtAc/hexanes 1% AcOH | 608 |
| 13 | Pr | n-Pn | COOi-Bu | 50% EtAc/hexanes 1% AcOH | 608 |
| 14 | Pr | $(CH_2)_3Ph$ | COOi-Bu | 50% EtAc/hexanes 1% AcOH | 656 |
| 15 | Pr | Bn | COOME | 50% EtAc/hexanes 1% AcOH | 586 |
| 16 | Pr | Bn | COOiBu | 40% EtAc/hexanes 1% AcOH | 628 |
| 17 | Pr | Bn | COOn-Pr | 50% EtAc/hexanes 1% AcOH | 614 |
| 18 | Pr | Bn | COOn-Bu | 50% EtAc/hexanes 1% AcOH | 628 |
| 19 | Pr | Bn | COOBN | 40% EtAc/hexanes 1% AcOH | 662 |
| 20 | Pr | Bn | COOn-Hx | 50% EtAc/hexanes 1% AcOH | 657 |
| 22 | Pr | Bn | $COO(CH_2)_2OMe$ | 75% EtOAC/hexanes 1% AcOH | 630 |
| 23 | Pr | $CH_2$c-Hx | COOPR | 50% EtAc/hexanes 1% AcOH | 620 |
| 24 | Pr | n-Bu | COOn-Bu | 40% EtAc/hexanes 1% AcOH | 594 |
| 25 | Pr | $(CH_2)_2OEt$ | $COO(CH_2)_2OMe$ | 50% EtAc/hexanes 1% AcOH | 612 |
| 26 | Pr | Bn | $SO_2Bu$ | 50% EtAc/hexanes 1% AcOH | 648 |
| 47 | Et | Me | COOi-Bu | 50% EtoAc/hexanes 1% AcOH | 538 |
| 48 | Et | Bn | COOi-Bu | 50% EtAc/hexanes 1% AcOH | 614 |
| 49 | i-Bu | Bn | COOi-Bu | 50% EtAc/hexanes 1% AcOH | 642 |
| 50 | i-Bu | Me | COOi-Bu | 50% EtAc/hexanes 1% AcOH | 566 |
| 51 | Me | Bn | COOi-Bu | 50% EtAc/hexanes 1% AcOH | 523 |
| 52 | Me | Me | COOi-Bu | 50% EtAc/hexanes 1% AcOH | 600 |
| 57 | Pr | Bn | COOET | 50% EtAc/hexanes 1% AcOH | 600 |
| 33 | Pr | Pn | COPH | 50% EtAc/hexanes 1% AcOH | 612 |
| 34 | Pr | Pn | COBN | 50% EtAc/hexanes 1% ACOH | 626 |
| 35 | Pr | Pn | COi-nicotinoyl | 100% EtAc/hexane 1% AcOH | 613 |
| 36 | Pr | Bn | COPh | 50% EtAc/hexane 1% AcOH | 632 |
| 37 | Pr | Pn | COPh(p-Cl) | 50% EtAc/hexane 1% AcOH | 646 |
| 38 | Pr | i-Hx | COPh(p-OMe) | 50% EtAc/hexane 1% ACOH | 656 |
| 39 | Pr | Pn | CO(2-Furyl) | 50% EtAc/hexane 1% AcOH | 602 |
| 41 | Pr | BnOBn | COi-Pn | 50% EtAc/hexane 1% AcOH | 732 |
| 42 | Pr | Bn | COn-Bu | 50% EtAc/hexane 1% AcOH | 612 |
| 43 | Pr | Pn | COPh(p-F) | 50% EtAc/hexane 1% AcOH | — |
| 44 | Pr | Bu | COPh(p-F) | 50% EtoAc/hexane 1% AcOH | — |
| 45 | Pr | Pn | COPh(p-Me) | 50% EtAc/hexane 1% AcOH | 626 |
| 46 | Pr | Pn | CO(m-Br) | 75% EtAc/hexane 1% AcOH | 692 |
| 54 | Pr | Bn(p-OH) | COiPn | 50% EtAc/hexane 1% AcOH | 642 |
| 55 | Pr | Bu | COBU | 50% EtAc/hexane 1% AcOH | 578 |

| Characteristic | $^1H$-NMR(CDCl$_3$- 400 MHz): |
|---|---|

For $R^5$ = carbamate

| | $R^4$ | $R^7$ |
|---|---|---|
| 3 | 4.92 (bs, 2H) | 3.91 (d, 2H, J = 7.3 Hz), 1.83 (m, 1H), 0.80 (d, 6H, J = 6.7 Hz). |
| 6 | 3.34 (s, 3H) | 1.25 (t, 3H, J = 7.0 Hz), 4.17 (q, 2H, J = 7.0 Hz). |
| 7 | 5.85 (m, 1H), 5.11 (m, 2H), 4.29 (d, 2H, J = 5.5 Hz). | 3.86 (d, 2H, J = 6.6 Hz), 1.92 (m, 1H), 0.83 (d, 6H, J = 6.6 Hz) |
| 8 | 3.33 (s, 3H) | 3.70 (t, 3H). |
| 9 | 3.33 (s, 3H) | 0.97 (t, 3H, J = 7.4 Hz), 1.32 (m, 2H), 1.59 (m, 2H, 4.10 (t, 2H, J = 6.7 Hz). |
| 10 | 3.69 (t, 2H, J = 7.4 Hz), 0.99 (t, 3H, J = 7.3 Hz) 1.52 (m, 2H), 1.29 (m, 2H) | 0.88 (t, 3H), 1.52 (m, 2H), 1.29 (m, 2H), 4.06 (t, 3H, J = 6.6 Hz) |
| 11 | | |
| 12 | 3.73 (t, 2H, J = 7.7 Hz), 1.43 (m, 2H), 1.55 (m, 1H), 0.86 (d, 6H) | 0.86 (d, 6H), 1.89 (m, 1H), 3.86 (d, 2H, J = 6.3 Hz) |
| 13 | 3.68 (t, J = 7.6 Hz), 1.59 (m, 2H) 0.85 (t, 3H) | 0.89 (d, 6H), 1.88 (m, 1H), 3.86 (d, 2H, J = 6.6 Hz). |
| 14 | 3.78 (t, 2H, = 7.3 Hz), 2.60 (t, 2H, J = 7.7 Hz), 0.85 (m, 2H) | 3.86 (d, 2H, J = 6.3 Hz), 0.85 (m, 1H), 0.84 (d, 6H, J = 6.2 Hz). |
| 15 | 4.91 (bs, 2H) | 3.71 (9s, 3H) |
| 16 | 4.94 (bs, 2H) | 3.91 (d, 2H, J = 6.4 Hz), 2.85 (m, 1H), 0.82 (d, 6H, J = 6.6 Hz) |
| 17 | 4.92 (bs, 2H) | 4.08 (t, 2H, J = 6.6 Hz), 1.58 (m, 2h), 0.83 (t, 3H, J = 7.3 Hz) |
| 18 | 4.94 (bs, 2H) | 4.14 (q, 2H), 1.55 (m, 2H), 1.29 (m, 2H), 0.86 (t, 3H, J = = 7.3 Hz). |
| 19 | 4.94 (bs, 2H) | 5.17 (bs, 2H). |
| 20 | 4.94 (bs, 2H) | 4.13 (t, 2H, J = 6.6 Hz), 1.60 (m, 4H), 1.22 (m, 4H), 0.82 (t, 3H, J = 6.9 Hz) |
| 22* | 4.97 (s, 2H) | 4.28 (t, 2H, J = 4.6 Hz), 3.54 (t, 2H, J = 4.6 Hz), 3.29 (s, 3H). |
| 23 | 3.59 (d, 2H, J = 7.3 Hz) | 4.03 (t, 2H, J = 6.6 Hz) |
| 24 | 3.71 (t, 2H, J = 7.3 Hz), 1.52 (m, 2H), 1.29 (m, 2H) 0.87 (t, 3H) | 4.08 (t, 2H, J = 6.2 Hz), 1.52 (m, 2H), 1.29 (m, 2H), 0.87 (t, 3H) |
| 25 | 3.5–3.6 (m, 4H), 3.42 (q, 2H, J = 7.0 Hz), 1.11 (t, 3H, J = 7.0 Hz) | 4.21 (bm, 2H), 3.85 (t, 2H, J = 5.8 Hz), 3.29 (bs, 3H). |
| 26 | 4.93 (bs, 2H) | 3.07 (m, 2H), 0.99 (t, 3H, J = 7.4 Hz) |

| | | |
|---|---|---|
| 47 | 3.35 (s, 3H) | 3.90 (m, 2H), 1.95 (m, 1H), 0.96 (d, 3H, J = 6.6 Hz), 0.88 (d, 3H, J = 6.3 Hz) |
| 48 | 4.92 (bs, 2H) | 3.91 (d, 2H, J = 6.5 Hz), 1.85 (m, 1H), 0.81 (d, 6H, J = 6.3 Hz) |
| 49 | 4.94 (s, 2H) | 3.91 (d, 2H, J = 6.6 Hz), 1.92 (m, 1H), 0.81 (d, 6H, J = 6.0 Hz) |
| 50 | 3.37 (s, 3H) | 3.91 (d, 2H, J = 6.7 Hz), 1.91 (m, 1H), 0.89 (3 line m, 6H, J = 6.8 Hz) |
| 51 | 3.34 (s, 3H) | 3.88 (d, 2H, J = 6.6 Hz), 1.89 (m, 1H), 0.86 (d, 6H, J = 6.3 Hz) |
| 52 | 4.93 (bs, 2H) | 3.90 (d, 2H, J = 6.5 Hz), 1.83 (m, 2H), 0.81 (d, 6H, J = 6.7 Hz) |
| 57 | 4.92 (s, 2H) | 4.18 (q, 2H, J = 7.1 Hz), 1.20 (t, 3H, J = 7.1 Hz). |

For $R^5$ = amide:

| | $R^4$ | $R^{10}$ |
|---|---|---|
| 33 | — | 3.90 (t, 2H, J = 8.0 Hz), 1.57 (m, 2H), 1.22 (m, 4H), 0.82 (t, 3H, J = 6.9 Hz) |
| 34 | 3.39 (bs, 2H) | 3.69 (t, 2H, J = 7.9 Hz), 1.45 (m, 2H), 1.21 (m, 4H), 0.81 (t, 3H, J = 7.0 Hz) |
| 35 | — | 3.95 (bm, 2H), 1.61 (bm, 2H), 1.30 (bm, 4H), 0.85 (t, 3H, J = 5.9 Hz) |
| 36 | 5.17 (s, 2H) | — |
| 37 | — | 3.91 (t, 2H, J = 8.0 Hz), 1.59 (m, 2H), 1.28 (m, 4H), 0.83 (bt, 3H, J = 6.8 Hz) |
| 38 | 2.01 (bm 2H), 1.40 (bm, 3H), 0.67 (d, 6H, J = 5.6 Hz) | 4.81 (bs, 2H), 3.72 (bs, 3H) |
| 39 | 5.87 (d, 1H, J = 2.6 Hz), 6.10 (dd, 1H, J 1.6, 3.46 Hz) | 3.86, (t, 2H, J = 7.7 Hz), 1.53 (bm, 2H), 1.25 (m, 4H), 0.82 (t, 3H, J = 6.3 Hz) |
| 41 | 2.02 (bt, 2H), 1.41 (m, 2H), 1.38 (m, 1H), 0.68 (d, 6H, J = 6.2 Hz) | 4.83 (bs, 2H), 4.97 (s, 2H). |
| 42 | 2.03 (bm, 2H), 1.51 (m, 2H), 1.16 (m, 2H), 4.89 (bs, 2H). 0.75 (t, 3H, J = 7.3 Hz) | |
| 43 | — | 3.88 (t, 2.H, J = 7.6 Hz), 1.57 (bm, 2H), 1.22 (m, 4H), 0.81 (t, 3H, J = 6.8 Hz) |
| 44 | — | 3.90 (t, 2H, J = 7.7 Hz), 1.55 (m, 2H), 1.29 (m, 2H), 0.85 (t, 3H, J = 7.5 Hz) |
| 45 | 2.17 (s, 3H) | 3.91 (t, 2H), 1.56 (m, 2H), 1.23 (m, 2H), 0.80 (bt, 3H). |
| 46 | — | 3.87 (t, 2H, J = 7.3 Hz), 1.55 (bm, 2H), 1.22 (m, 4H), 0.81 (t, 3H, j = 7.2 Hz) |
| 54 | 2.02 (bt, 2H), 1.42 (bm, 2H), 1.35 (m, 1H), 0.69 (d, 6H, J = 6.2 Hz) | 4.79 (bs, 2H) |
| 55 | not assigned: 2.02 (bt, J = 7.6 Hz), 1.45 (bm, 4H), 1.26 (m, 2n), 1.12 (m, 2H), 1.01 (t, 3H, J = 7.3 Hz), 0.73 (t, 3H, J = 6.9 Hz). | |

PREPARATION OF EXAMPLE 54

Preparation of 6-(N-(4-hydroxybenzyl)-N-(3-methyl-butanoyl))-amino-2-n-propyl-3-[(2'-(tetrazol-5-yl)-biphen-4-yl)-methyl]-quinazolin-4(3H)-one 0.036 g (0.05 mmol) of Example 41 was hydrogenated in 1.5 ml of EtOAc in the presence of 15 mg of 10% Pd/C at atmospheric pressure for 24 hours. The reaction mixture was filtered through celite and concentrated in vacuo. The residue was purified by flash chromatography over silica gel eluting with 50% EtOAc/hexanes 1% AcOH to give 16.6 mg (0.026 mmol) of the desired product. 51% yield.

By following a similar synthetic approach Examples 130, 131, 144 and 147 were prepared.

PREPARATION OF EXAMPLE 4

6-(N-Methyl-N-t-butoxycarbonyl)-amino-2-n-butyl-3-[(2'-(tetrazol-5-yl)-bipen-4-yl)-methyl]-quinazolin-4(3H)-one

Step 1

2-n-Butyl-3-[(2'-(N-triphenylmethyl-tetrazol-5-yl)-biphen-4-yl)-methyl]-6-(N-carbobenzyloxy)-amino-quinazolin-4(3H)-one To a suspension of 4 mg (0.12 mmol) of 80% NaH in oil in 1 mL of dry DMF under nitrogen was added at 0° C. a solution of 69 mg (0.1 mmol) of 6-Amino-2-n-butyl-3-[(2'-(N-triphenylmethyl-tetrazol-5-yl)-biphen-4-yl)-methyl]-quinazolin-4(3H)-one. A bright blue solution was formed. After 0.5 hours 18.8 mg (0.1 mmol) of benzylchloroformate was added via syringe. The blue colour rapidly dissipated and the reaction mixture was stirred for 3 hours while allowing the temperature to rise to room temperature. The reaction mixture was concentrated in vacuo and the residue was dissolved in 25 ml of EtOAc and 5 mL of water. The aqueous phase was extracted with EtOAc (2×5 ml) and the combined organic phases were washed with water (1×5 ml), brine (1×5 ml) and dried over MgSO$_4$. The mixture was filtered and concentrated in vacuo and the residue was purified by flash chromatography over silica gel eluting with 30% EtOAc/hexane to give 51.7 mg (0.62 mmol) of the title compound. $^1$H-NMR (CDCl$_3$-300 MHz): 0.88 (t, 3H, J=7.3 Hz), 1.32 (m, 2H), 1.68 (m, 2H), 2.60 (3 line m, 2H, J=8.41 Hz), 5.19 (s, 2H), 5.29 (bs, 2H), 6.90 (m, 8H), 7.09 (d, 1H, J=8.2 Hz), 7.2–7.52(m, 18H), 7.65 (d, 1H, J=8.8 Hz), 7.91 (m, 1H), 8.19 (m, 2H).

Step 2

2-n-Butyl-3-[(2'-(N-triphenylmethyl-tetrazol-5-yl)-biphen-4-yl)-methyl]-6-(N-carbobenzyloxy-N-methyl)-amino-quinazolin-4(3H)-one To a suspension of 20 mg (0.65 mmol) of 80% NaH in mineral oil in 2 mL of dry DMF at 0° C. under nitrogen was added a solution of 0.49 g (0.59 mmol) of 2-n-Butyl-3-[(2'-(N-triphenylmethyl-tetrazol-5-yl)-biphen-4-yl)-methyl]-6-(N-carbobenzyloxy)-amino-quinazolin-4(3H)-one in 4 mL of DMF. A blue solution formed on consumption of the NaH. The reaction mixture was allowed to stir for 90 minutes at which time 0.04 mL (0.6 mmol) of methyl iodide was added. The ice bath was removed and the reaction mixture was stirred for a further 45 minutes. To the reaction mixture was added 1 mL of water and the reaction mixture was concentrated in vacuo. The residue was dissolved in 50 ml of EtOAc and the organic phase was washed with water (2×20 ml) and brine (1×20 ml). The mixture was dried over MgSO$_4$, filtered and concentrated in vacuo. The residue was purified by flash chromatography over silica gel eluting with 30% EtOAc/hexane to give 0.44 g (0.52 mmol) of an orange solid. 89% yield. $^1$H-NMR (CDCl$_3$-300 MHz): 0.88 (t, 3H, J=7.3 Hz), 1.32 (m, 2H), 1.69 (m, 2H), 2.65 (3 line m, 2H, J=8.2 Hz), 3.40 (s, 3H), 5.19 (s, 2H), 5.29 (bs, 2H), 6.92 (m, 8H), 7.09 (d, 2H, J=8.1 Hz) 7.2–7.37 (m, 15H), 7.46 (m, 2H), 7.62 (d, 1H), 7.72 (m, 1H), 7.91 (d, 1H), 8.12 (d, 1H).

Step 3

6-(N-Methyl)-amino-2-n-butyl-3-[(2'-(N-triphenylmethyl-tetrazol-5-yl)-biphen-4-yl)-methyl]-quinazolin-4(3H)-one A solution of 0.78 g (0.94 mmol) of 2-n-Butyl-3-[(2'-(N-triphenylmethyl-tetrazol-5-yl)-biphen-4-yl)-methyl]-6-(N-carbobenzyloxy-N-methyl)-amino-quinazolin-4(3H)-one was dissolved in 20 ml of EtOAc and hydrogenated under atmospheric pressure in the presence of 0.1 g of 10% Pd/C. After stirring for 18 hours the solution was filtered through celite and concentrated in vacuo. The residue was not purified further. Recovered 0.66 g (0.94 mmol). 100% yield. $^1$H-NMR (CDCl$_3$):0.89 (t, 3H), 1.42 (m, 2H), 1.69 (m, 2H), 2.62 (3 line m, 2H), 2.95 (s, 3H), 5.30 (bs, 2H), 6.88–6.98 (m, 8H), 7.09 (m, 4H), 7.21–7.38 (m, 9H), 7.45 (m, 4H), 7.91 (dd, 1H).

Step 4

6-(N-Methyl-N-t-butoxycarbonyl)-amino-2-n-butyl-3-[(2'-(N-triphenylmethyl-tetrazol-5-yl)-biphen-4-yl)-methyl]-quinazolin-4(3H)-one To a solution of 0.14 g (0.21 mmol) of 6-(N-Methyl)-amino-2-n-butyl-3-[(2'-(N-triphenylmethyl-tetrazol-5-yl)-biphen-4-yl)-methyl]-quinazolin-4(3H)-one in 2.5 ml of dry CH$_2$Cl$_2$ was added 26 mg (0.26 mmol) of triethyl amine, 32 mg (0.26 mmol) of dimethyl amino pyridine and 11.5 mg (0.52 mmol) of t-butoxy carbonyl anhydride. The solution was heated to reflux under N$_2$ overnight. A further quantity of triethyl amine, and t-butoxy carbonyl anhydride was added as above and heating continued for a further 18 hours. The reaction mixture was concentrated in vacuo and purified by flash chromatography to give 0.091 g (0.11 mmol) of a colorless oil. 52% yield. $^1$H-NMR (CDCl$_3$):0.89 (t, 3H, J=7.4 Hz), 1.32 (m, 2H), 1.25 (s, 9H), 1.70 (m, 2H), 2.65 (3 line m, 2H, J=7.9 Hz), 3.35 (s, 3H), 5.30 (bs, 2H), 6.89–6.98 (m, 8H), 7.09 (d,2H, J=8.2 Hz), 7.22–7.35 (m, 10H), 7.46 (m, 2H), 7.62 (d, 1H, J=8.8 Hz), 7.73 (dd, 1H, J=6.4, 2.4 Hz), 7.92 (dd, 1H, J=2.1, 6.3 Hz), 8.09 (d, 1H, J=2.5 Hz).

Step 5

6-(N-Methyl-N-t-butoxycarbonyl)amino-2-n-butyl-3-[(2'-(tetrazol-5-yl)biphen-4-yl)-methyl]quinazolin-4(3H)-one 0.091 (0.11 mmol) of 6-(N-Methyl-N-t-butoxycarbonyl)-amino-2-n-butyl-3-[(2'-(N-triphenylmethyl-tetrazol-5-yl)-biphen-4-yl)-methyl]-quinazolin-4(3H)-one was stirred for 6 hours with 5 ml of a mixture of 3:1:1 acetic acid:water:THF at room temperature. The product was purified by flash chromatography over silica gel eluting with 50% EtOAc/hexanes and 1% acetic acid. Recovered 0.04 g 64% yield. $^1$H-NMR (CDCl$_3$): 0.91 (t, 3H, J=7.3 Hz), 1.40 (m, 2H), 1.45 (s, 9H), 1.72 9m, 2H), 2.72 (3 line m, 2H, J=7.9 Hz), 3.29 (s, 3H), 5.33 (bs, 2H), 7.08 (s, 3H), 7.16 (d, 1H, J=7.3 Hz), 7.25 (t, 1H, J=7.8 Hz), 7.37 (d, 1H, J=7.4 Hz), 7.49–7.58 (m, 3H), 7.69 (dd, 1H, J=2.1, 8.5 Hz), 7.94 (d, 1H, J=7.5 Hz), 7.99 (d, 1H, J=2.4 Hz). FABMS=565 for M$^+$+1.

PREPARATION OF EXAMPLE 21

Step 1

6-(N-benzyl)-amino-2-n-propyl-3-[(2'-(N-triphenylmethyl-tetrazol-5-yl)-biphen-4-yl)-methyl]-quinazolin-4(3H)-one To a suspension of 0.5 g (0.74 mmol) of 6-Amino-2-n-propyl-3-[(2'-(N-triphenylmethyl-tetrazol-5-yl)-biphen-4-yl)-methyl]-quinazolin-4(3H)-one in 5 ml of dry EtOH was added 1.5 ml of CH$_2$Cl$_2$ and 0.4 g (3.7 mmol) benzaldehyde and 0.5 g of 3A° activated ground molecular sieves. After 1 hour 0.23 g (3.7 mmol) of sodium cyanoborohydride was added. The reaction mixture was stirred over night. The reaction mixture was diluted with 50 ml of EtOAc and washed with water (3×10 ml), brine (1×10 ml) and dried over MgSO$_4$. The mixture was filtered and the residue was purified by flash chromatography over silica gel eluting with 30% EtOAc hexanes to give 0.2 g (0.26 mmol) of the product. 36% yield. $^1$H-NMR (CDCl$_3$): 0.93 (t, 3H, J=7.3 Hz), 1.73 (m, 2H), 2.59 (3 line m, 2H, J=7.8 Hz), 4.39 (bm, 1H), 4.42 (bs, 2H), 5.28 (bs, 2H), 6.86–6.98 (m, 8H), 7.05–7.12 (m, 4H), 7.19–7.55 (m, 20H), 7.92 (dd, 1H, J=2.5 Hz).

Step 2

6-(N-benzyl)-amino-2-n-propyl-3-[(2'-(N-triphenylmethyl-tetrazol-5-yl)-biphen-4-yl)-methyl]-quinazolin-4(3H)-one was submitted sequentially to the conditions described for the preparation of 6-(N-Methyl-N-t-butoxycarbonyl)-amino-2-n-butyl-3-[(2'-(N-triphenylmethyl-tetrazol-5-yl)-biphen-4-yl)-methyl]-quinazolin-4(3H)-one and the deprotection to give Example 4 to give the desired product after purification by flash chromatography over silica gel eluting with 50% EtOAc/hexanes and 1% acetic acid. $^1$H-NMR (CDCl$_3$): 0.96 (3H, t, J=7.4 Hz), 1.39 (s, 9H), 1.75 (m, 2H), 2.67 (3 line m, 2H, J=7.7 Hz), 4.87 (s, 2H), 5.27 (bs, 2H), 7.06 (s, 4H), 7.15–7.28 (m, 5H), 7.35 (d, 1H, J=7.6 Hz), 7.45–7.55 (m, 5H), 7.90 (dd, 1H, J=1.1, 7.7 Hz), 7.99 (d, 1H, J=1.8 Hz). FABMS: 628 for M$^+$+1.

PREPARATION OF EXAMPLE 2

To a solution of 0.1 g (0.12 mmol) of 2-n-Butyl-3-[(2'-(N-triphenylmethyl-tetrazol-5-yl)-biphen-4-yl)-methyl]-6-(N-carbobenzyloxy)-amino-quinazolin-4(3H)-one and 0.097 g (0.13 mmol) of isopropyl methyl amine in 3 ml of dry THF was added at 0° C. under N$_2$ 0.044 ml of a 3M solution of methyl magnesium bromide in THF. The solution was heated to 80° C. for 2 hours, cooled to room temperature, and treated cautiously with 10 ml of H$_2$O. The resulting mixture was extracted with EtOAc (3×10 ml). The combined organic extracts were washed with water (1×5 ml), brine (1×5 ml) and dried over MgSO$_4$ The mixture was filtered, concentrated in vacuo and purified by flash chromatography over silica gel eluting with 50% EtOAc/hexanes to give an oil which was then alkylated with methyl iodide as descibed in the general experimental outline for the synthesis of Examples 29, 30 and 31 and was then purified by flash chromatography over silica gel eluting with 50% EtOAc/hexanes to give the tetrasubstituted urea. The trityl protected tetrazole was deprotected in the general manner described above and the product was purified by flash chromatography over silica gel eluting with 60% EtOAc/hexanes 1% acetic acid to give the title compound. $^1$H-NMR (CDCl$_3$-400 MHz): 0.92 (t, 3H, J=7.3 Hz), 1.04 (d, 6H, J=6.7 Hz), 1.42 (m, 2H), 1.75 (d, 2H), 2.46 (s, 3H), 2.77 (t, 3H, J=7.8 Hz), 3.19 (s, 3H), 4.29 (m, 1H), 5.39 (bs, 2H), 7.12 (m, 4H), 7.39 (m, 2H), 7.55 (m, 3H), 7.90 (d, 1H, J=2.1 Hz), 7.99 (d, 1H, J=6.5 Hz).

PREPARATION OF EXAMPLES 29, 30 AND 31

6-(N-Carbobenzyloxy)-amino-2-n-propyl-3-[(2'-(N-triphenylmethyl-tetrazol-5-yl)-biphen-4-yl)-methyl]-quinazolin-4(3H)-one was prepared as described for the 2-n-butyl case above. This derivative was then commited to reaction with N-propyl methyl amine, ethyl methyl amine and bis-n-pentyl amine under the reaction conditions described for Example 2 to give the appropriate ureas. The ureas were then alkylated at the aniline amine in the following manner:

To a solution of 0.022 mmol of the urea in 1.5 ml of dry DMF at 0° C. under nitrogen was added 0.25 mmol of a 1M solution of lithium hexamethyl disilazide in THF. After 30 minutes 0.088 mmol of the desired alkylating agent (benzyl bromide or methyl iodide) was added neat. The reaction mixture was stirred at room temperature over night, diluted with 30 ml of EtOAc and washed with water (3×5 ml), brine (1×5 ml) and dried over MgSO$_4$. The mixture was filtered, concentrated in vacuo and the residue was purified by flash chromatography eluting with an appropriate mixture of EtOAc/hexanes to give approximately 80% yields of the desired tetrasubstituted ureas. The ureas were de-protected utilizing the general protocol described above and purified by flash chromatography over silica gel and characterised as follows:

EXAMPLE 29

Elution solvent: 70% EtOAc/hexanes 1% acetic acid. $^1$H-NMR (CDCl$_3$): 0.77 (t, 3H, J=7.5 Hz), 0.98 (t, 3H, J=7.4 Hz), 1.45 (m, 2H), 1.78 (m, 2H), 2.61 (s, 3H), 2.69 (3 line m, 2H, J=8.2 Hz), 3.11 (t, 2H, J=7.4 Hz), 4.85 (s, 2H), 5.34 (bs, 2H), 7.10–7.38 (m, 12H), 7.86 (d, 1H, J=2.7 Hz), 8.01 (d, 1H), J=7.5 Hz). FABMS=627 (M$^+$+1).

EXAMPLE 30

Elution solvent: 75% EtOAc/hexanes 1% acetic acid. $^1$H-NMR (CDCl$_3$):1.05 (m, 6H), 1.79 (m, 2H), 2.64 (s, 3H), 2.78 (m, 2H), 3.25 (q, 2H, J=6.9 Hz), 4.91 (s, 2H), 5.35 (bs, 2H), 6.88 (d, 2H, J=7.6 Hz), 7.05–7.62 (m, 12H), 7.85 (d, 1H, J=2.2 Hz), 8.05 (d, 1H, J=7.3 Hz). FABMS=613 (M$^+$+1)

EXAMPLE 31

Elution solvent: 60% EtOAc/hexanes 1% acetic acid. $^1$H-NMR (CDCl$_3$):.0.81 (t, 6H, J=7.2 Hz), 0.98 (t, 3H, J=7.4 Hz), 1.06–1.28 (m, 8H), 1.40 (m, 4H), 1.76 (m, 2H), 2.68 (3 line m, 2H, J=7.6 Hz), 3.13 (s, 3H), 5.34 (bs, 2H), 7.02–7.12 (m, 4H), 7.38 (m, 2H), 7.51 (m, 3H), 7.88 (m, 2H). FABMS=635 (M$^+$+1).

PREPARATION OF EXAMPLE 53

Step 1

3-(4,4'-Dimethoxybenzhydryl)-6-(N-methyl-N-isobutyrylcarbamoyl)-amino-2-propyl-quinazolin-4(3H)-one To a suspension of 81.5 mg (2.7 mmol) of 80% NaH in 3 ml of dry DMF at 0° C. under nitrogen was added dropwise a solution of 1.03 g (2.5 mmol) of 6-amino-3-(4,4'-dimethoxybenzhydryl)-2-propyl-quinazolin-4(3H)-one dissolved in 3 ml of DMF. The resulting mixture was stirred for 30 minutes and was then treated with 0.35 ml (2.7 mmol) of isobutylchloroformate neat. The solution was stirred for 30 minutes and then treated with 2.97 ml (2.97 mmol) of a 1M solution of lithium hexamethyldisilazide in THF. The dark solution was stirred for a further 30 minutes at 0° C. and then was treated with 0.2 ml (3.26 mmol) of iodomethane neat. The mixture was stirred overnight at room temperature, poured into 50 ml of EtOAc and washed consecutively with water (2×10 ml), brine (1×10 ml) and dried over MgSO$_4$. The product was purified by flash chromatography over silica gel eluting with 30% EtOAc/hexanes to give 0.9 g (1.7 mmol) of an oil. 71% yield. $^1$H-NMR (CDCl$_3$): 0.82–0.91 (m, 6H), 0.96 (d, 3H, J=6.8 Hz), 1.52 (m, 2H), 1.88 (m, 1H), 2.67 (bt, 2H), 3.35 (s, 3H), 3.80 (s, 6H), 3.90 (d, 2H, J=6.6 Hz), 6.87 (d, 4H, J=8.8 Hz), 7.20 (d, 4H, J=8.8 Hz), 7.61 (m, 1H), 7.78 (m, 1H), 8.01 (d, 1H, 2 Hz).

Step 2

6-(N-methyl-N-isobutyrylcarbamoyl)-amino-2-propyl-quinazolin-4(3H)-one 0.9 g (1.7 mmol) of 3-(4,4'-Dimethoxybenzhydryl)-6-(N-methyl-N-isobutyrylcarbamoyl)-amino-2-propyl-quinazolin-4(3H)-one was added to a mixture of 3.0 ml of a 10:1 mixture of trifluoroacetic acid and anisole. The solution was stirred for 4 hours, concentrated in vacuo and the residue was purified by flash chromatography over silica gel eluting with 50% EtOAc/hexanes to give 0.47 g (1.5 mmol) of a white solid. 88% yield. $^1$H-NMR (CDCl$_3$): 0.89 (d, 6H, J=6.7 Hz), 1.07 (t, 3H, J=7.4 Hz), 1.92 (m, 2H), 2.76 (t, 2H, J=7.8 Hz), 3.40 (s, 3H), 3.93 (d, 2H, J=6.6 Hz), 7.70 (m, 2H), 8.10 (d, 1H, J=2.6 Hz).

Step 3

3-((2'-tert-butylaminosulfonyl)(1,1'-biphenyl)-4-yl)-methyl-6-(N-methyl-N-isobutyloxycarbonyl)-amino-2-propyl-quinazolin-4-one To a suspension of 80% NaH (11.5 mg, 0.38 mmol) in dry DMF (3 ml) at 0° C. under nitrogen was added 6-(N-methyl-N-isobutyloxycarbonyl)-amino-2-propyl-quinazolin-4(3H)-one (0.1 g, 0.32 mmol) as the solid. The resulting mixture was stirred for 30 minutes and then added 4'-bromomethylbiphenyl-2-tert-butylsulfonamide (0.122 g, 0.35 mmol) as the solid. The solution was stirred for 30 minutes at 0° C. and then overnight at room temperature. The reaction mixture was diluted with EtOAc (50 ml) and washed consecutively with water (2×10 ml), brine (1×10 ml) and dried over MgSO$_4$. The product was purified by flash chromatography over silica gel eluting with 25% EtOAc/hexanes to give 0.15 g (75%) of the desired product as an oil. $^1$H-NMR (CDCl$_3$): 0.88 (d, J=6.6 Hz,6H), 0.95 (s, 9H), 1.05 (d, J=7.4 Hz 3H), 1.85 (m, 3H), 2.67 (bt, 2H), 3.35

(s, 3H), 3.90 (d, 2H, J=6.6 Hz), 5.42 (s,2H), 7.32 (m, 2H), 7.4–7.64 (m, 5H), 7.7 (bm, 1H), 7.95–8.10 (m, 2H), 8.16 (dd, J=7.5, 1.6 Hz,1H).

Step 4

3-((2'-aminosulfonyl)(1,1'-biphenyl)-4-yl)methyl-6-(N-methyl-N-isobutyloxycarbonyl)-amino-2-propyl-quinazolin-4-one A solution of 3-((2'-tert-butylaminosulfonyl)(1,1'-biphenyl)-4-yl)methyl-6-(N-methyl-N-isobutyloxycarbonyl)-amino-2-propyl-quinazolin-4-one (0.148 g, 0.24 mmol) and anisole (0.05 ml) in trifluoroacetic acid (3 ml) was stirred at room temperature for 6 h. The reaction mixture was concentrated in vacuo, and the residue was dissolved in ethylacetate (25 ml) and washed consecutively with saturated bicarbonate solution (5 ml), water (2×5 ml) and brine (10 ml) and dried over MgSO4. Removal of the solvent in vacuo gave the desired product (0.119 g) as a foam. $^1$H-NMR (CDCl$_3$): 0.88 (d, J=6.6 Hz,6H),1.05 (d, J=7.4 Hz 3H), 1.85 (m, 3H), 2.67 (bt, 2H), 3.35 (s, 3H), 3.90 (d, 2H, J=6.6 Hz), 5.42 (s,2H), 7.26–7.64 (m, 6H), 7.81–8.18 (m, 6H).

Step 5

3-[(2'-(N-benzoyl)sulfonamidomethylbipheny-4-yl)-methyl]-6-(N-methyl-N-isobutyrylcarbamoyl)-amino-2-propyl-quinazolin-4-one To a solution of 3-((2'-aminosulfonyl) (1,1'-biphenyl)-4-yl)methyl-6-(N-methyl-N-isobutyryl-carbamoyl)-amino-2-propyl-quinazolin-4-one (0.043 g, 0.0764 mmol) in dry pyridine (2 ml) was added benzoyl chloride (0.045 ml) and resuting mixture was stirred at room temperature for 20 h. The reactin sovent was removed in vacuo, and the residue was dissolved in ethylacetate (50 ml) and washed with 5% aqueous citric acid (2×5 ml), water (10 ml) and brine (10 ml) and then dried over MgSO4. The crude product, obtained after removal of the solvent in vacuo, was purified by flash chromatography over silica gel eluting with 2% MeOH/CH$_2$Cl$_2$ to give the desired product (0.035 g) as a cream colored solid. $^1$H-NMR (CDCl$_3$): 0.88 (d, J=6.6 Hz,6H), 1.02 (d, J=7.4 Hz 3H), 1.83 (m, 3H), 2.65 (bt, 2H), 3.37 (s, 3H), 3.90 (d, 2H, J=6.6 Hz), 5.45 (s,2H), 7.2–7.3 (m, 4H), 7.41–7.78 (m, 8H), 8.08 (s,1H), 8.14 (dd, J=7.5, 1.6 Hz,1H).

Preparation of Example 104

Example 104 was prepared by following Route F Scheme 3 with changes in the reagents. In place of 4'-bromomethylbiphenyl-2-tert-butyl-sulfonamide was used 4'-bromomethyl-2-nitro-biphenyl as the alkylating agent. The 6-pentylaminoquinazolinone was subsequently acylated as in Scheme 1 Step a and the nitro group reduced to the amine as in Scheme 1 Step f. The amino biphenyl was then acylated in the following manner: To a solution of 0.08 g (0.15 mmol) of 2-propyl-6-(N-pentyl-N-benzoyl)-amino-3-[(2'-amino-biphen-4-yl)-methyl]-quinazolin-4(3H)-one in 1.5 ml of CH$_2$Cl$_2$ was added 38 mg (0.18 mmol) of 2,6-di-t-butyl-4-methyl-pyridine followed by 28 mg (0.16 mmol) of triflic anhydride. The reaction mixture was stirred for two hours and diluted with 50 ml EtOAc and washed with water (3×10 ml), brine (1×10 ml) and was dried over MgSO4. The suspension was filtered and concentrated in vacuo and the residue was purified by flash chromatography over silica gel eluting with 95:5:0.5 CH$_2$Cl$_2$/MeOH/NH$_4$OH to give 52.8 mg of the desired triflamide. 1H-NMR (CDCl$_3$-400 MHz): 0.84 (t, 3H, J=6.96 Hz), 1.28 (m, 4H), 1.61 (m, 2H), 0.80 (m, 2H), 2.71 (t, 2H, J=7.61 Hz), 3.94 (t, 2H, 7.7 Hz), 5.39 (bs, 2H), 7.1–7.32 (m, 14H), 7.37 (t, 1H, J=7.3 Hz), 7.46 (8.7 Hz), 7.57 (d, 1H, J=8.06 Hz), 8.03 (d, 1H, J=2.5 Hz).

Preparation of Example 149

Step 1

To a solution of 0.2 g (0.23 mmol) of the product of the example 144 prior to deprotection of the tetrazole in 2.5 ml of THF under N$_2$ at 0° C. was added 0.26 ml (0.26 mmol) of a 1M solution of sodium hexamethyldisilazide in THF. After a period of 5 minutes a solution of 0.16 g (0.29 mmol) of tetrabenzylpyrophosphate was added in 1 ml of THF. The reaction mixture was stirred over night at room temperature, diluted with 50 ml of EtOAc and washed with water (3×10 ml) and brine (1×10 ml). The solution was dried over MgSO4, filtered and concentrated in vacuo. The residue was purified by radial chromatography over silica gel eluting with 2% MeOH/CH$_2$Cl$_2$ to give 0.22 g of a colorless oil. 84% yield. $^1$H-NMR (CDCl$_3$-400 MHz): 0.91 (m, 6H), 1.32 (m, 2H), 1.61 (m, 2H), 1.72 (m, 2H), 2.59 (t, 2H, J=8.01 Hz), 3.95 (t, 2H, J=7.4 Hz), 4.99 (s, 2H), 5.02 (s, 2H), 5.22 (s, 2H), 6.88–6.98 (m, 10H), 7.08 (d, 2H, J=8.3 Hz), 7.20–7.37 (m, 23H), 7.45 (m, 3H), 7.91 (m, 1H), 8.04 (d, 1H, J=2.5 Hz).

Step 2

The trityl protecting group of the product of Step 1 was removed by stirring with 3 ml of 3:1:1 acetic acid:-water:THF at room temperature over night. The reaction mixture was concentrated in vacuo and the residue was purified by radial chromatography over silica gel eluting with 70:30:1 EtOAc:hexanes:acetic acid to give 0.1 g of an oil: $^1$H-NMR (CDCl$_3$-400 MHz): 0.86 (t, 3H, J=7.4 Hz), 0.94 (t, 3H, J=7.3 Hz), 1.30 (m, 2H), 1.54 (m, 2H), 1.72 (m, 2H), 2.64 (t, 2H, J=7.4 Hz), 3.92 (t, 2H, J=7.7 Hz), 4.92 (s, 2H), 4.95 (s, 2H), 5.26 (bs, 2H), 6.85 (d, 2H, J=8.50 Hz), 6.99–7.52 (m, 19H), 7.73 (dd, 1H, J=1.3, 7.7 Hz), 7.96 (d, 1H, J=2.6 Hz).

Step 3

0.17 g (0.2 mmol) of the dibenzyl phosphate from Step 2 was hydrogenated over night at atmospheric pressure in 3 ml of dioxane in the presence of 0.6 ml (0.6 mmol) of a 1M solution of sodium bicarbonate and a catalytic quantity of 10% Pd/C. The reaction mixture was filtered and concentrated in vacuo to give 0.14 g of a colorless powder. Analysis by HPLC:Dynamax C18 analytical column 1 ml/min 15% H$_2$O/CH$_3$CN 0.1% TFA detected at 254 nM retention time of 4.9 min 98% pure. $^1$H-NMR (CD$_3$OD-400 MHz): 0.92 (t, 3H, J=7.3 Hz), 0.95 (t, 3H, J=4.8 Hz), 0.39 (m, 2H), 1.62 (m, 2H), 1.72 (m, 2H), 2.71 (t, 2H, J=8.0 Hz), 3.97 (t, 2H, J=7.9 Hz), 5.37 (bs, 2H), 7.02–7.27 (m, 8H), 7.40–7.57 (m, 6H), 7.98 (d, 1H, J=2.1 Hz).

By following an analogous synthetic route Examples 143 and 146 may be prepared.

Preparation of Example 81

To a solution of 0.05 g (0.07 mmol) of Example 77 in 1 ml of acetic acid at 0° C. was addded 0.009 ml (0.08 mmol) of a 30% solution of H$_2$O$_2$. The reaction mixture was stirred under N$_2$ for 6 hours, concentrtated in vacuo and the residue was purified by flash chromatography over silica gel eluting with 50% EtOAC/30% hexanes/20% MeOH/1% acetic acid to give 18 mg of the desired product. $^1$H-NMR (CD$_3$OD-400 MHz): 0.89 (t, 3H, J=6.6 Hz), 0.94 (t, 3H, J=7.4 Hz), 1.32 (m, 4H), 1.60-1.77 (m, 4H), 2.68 (s, 3H), 2.70 (t, 2H, J=7.5 Hz), 4.01 (t, 2H, J=6.7 hz), 5.33 (bs, 2H), 7.06 (m, 4H), 7.45 (d, 2H, J=7.1 Hz), 7.51-7.62 (m, 8H), 7.92 (s, 1H).

Preparation of Example 83

To a solution of 0.05 g (0.076 mmol) of Example 77 was added in 2 ml of acetic acid 0.03 ml (0.3 mmol) of 30% H$_2$O$_2$. The reaction mixture was stirred over night at room temperature, concentrated in vacuo and the residue was purified by flash chromatography over silica gel eluting with 75% EtOAc/25% hexanes/1% acetic acid to give 0.02 g of the desired sulfone. $^1$H-NMR (CDCl$_3$-200 MHz): 0.85 (t, 3H), 0.97 (t, 3H), 1.20-1.40 (m, 4H), 1.61 (m, 2H) 1.79 (m, 2H), 2.72 (t, 3H, J=8.1 Hz), 2.95 (s, 3H), 3.95 (t, 2H, J=7.81 Hz), 5.31 (bs, 2H), 7.05 (bs, 4H), 7.30-7.60 (m, 7H), 7.72 (d, 2H, J=8.2 Hz), 7.87 (d, 1H, J=7.3 Hz), 7.97 (d, 1H, J=2.0 Hz).

Preparation of Example 82

Following route B2B utilizing 2(2-bromoethyl)-1,3-dioxolane as the alkylating agent the intermediate 2-n-propyl-3-[(2'-(N-triphenylmethyl-tetrazol-5-yl)-biphen-4-yl)-methyl]-6-(N-benzoyl-N-(ethyl-1,3-dioxolanyl))-amino-quinazolin-4(3H)-one was prepared. 0.17 g of this intermediate was stirred in a mixture of 2 ml of THF 0.5 ml of water and 5 drops of concentrated HCl. The reaction mixture was concentrated in vacuo and the residue was dissolved in 20 ml of CH$_2$Cl$_2$ and washed with brine and was dried over MgSO$_4$. The suspension was filtered and concentrated in vacuo and the residue was purified by flash chromatography over silica gel eluting with 85% EtOAc/hexanes 1% aceitc acid to give 0.08 g of the product. $^1$H-NMR (CDCl$_3$-400 MHz): 0.89 (t, 3H), 1.72 (m, 2H), 2.69 (t, 2H), 2.80 (t, 2H), 4.21 (t, 2H), 5.28 (bs, 2H), 7.0-7.52 (m, 14H), 7.77 (d, 1H), 8.01 (d, 1H), 9.72 (d, 1H).

Preparation of Example 105

To a solution of Example 103 in 2 ml of MeOH was added 0.4 ml of 1N NaOH followed by 1 ml of water. The reaction mixture was warmed to 50° C. until such time that all the starting material had been consumed. The reaction mixture was diluted with EtOAc (15 ml) and washed with 10% citric acid (1×5 ml), brine (1×5 ml) and was dried over MgSO$_4$. The suspension was filtered and concentrated in vacuo and the residue was was not purified further. $^1$H-NMR (CDCl$_3$-400 MHz): 0.94 (t, 3H, J=7.3 Hz), 1.72 (m, 2H), 1.91 (m, 2H), 2.38 (t, 2H, J=6.96 Hz), 2.68 (t, 2H, J=7.2 Hz), 4.00 (t, 2H, J=7.0 Hz), 5.29 (bs, 2H), 7.0-7.25 (m, 10H), 7.33 (d, 1H, J=7.4 Hz), 7.43 (m, 2H), 7.52 (t, 2H, J=7.3 Hz), 7.79 (d, 1H, J=7.3 hz), 8.16 (s, 1H). 10.0 (bs, 1H).

Example 120 was prepared in an analogous manner.

Preparation of Example 132

2-n-propyl-3-[(2'-(N-triphenylmethyl-tetrazol-5-yl)-biphen-4-yl)-methyl]-6-(N-benzl-N-(2-bromoacetyl)-amino-quinazolin-4(3H)-one was prepared following the general route B3. 0.1 g (0.11 mmol) of the intermediate bromide was then added to 0.2 mmol of the sodium salt of imidazole generated in 1 ml of dry DMF with NaH at room temeprature. The reaction mixture was stirred over night. The reaction mixture was diluted with EtOAc (20 ml) and washed with water (2×5 ml) and brine (1×5 ml) and was dried over MgSO$_4$. The suspension was filtered and concentrated in vacuo and the residue was purified by flash chromatography over silica gel eluting with 3% MeOH/CH$_2$Cl$_2$ to give 0.09 g of the N-imidazolyl derivative. The trityl protecting group was removed in the general manner described above to give following purification by flash chromatography over silica gel eluting with 6% MeOH/CH$_2$Cl$_2$ the desired product. $^1$H-NMR (CD$_3$OD-400 MHz): 0.96 (t, 3H, J=7.4 Hz), 1.73 (m, 2H), 2.74 (t, 2H, J=7.6 Hz), 4.83 (s, 2H), 4.99 (s, 2H), 5.36 (bs, 2H), 7.05 (dd, 4H), 7.21 (s, 4H), 7.43 (m, 2H), 7.53 (m, 2H), 7.62 (dd, 1H, J=8.7, 2.2 Hz), 7.70 (d, 1H, J=8.7 Hz), 8.12 (s, 1H).

Example 133 was prepared via an analogous route by alkylating 2-n-propyl-3-[(2'-(N-triphenylmethyl-tetrazol-5-yl)-biphen-4-yl)-methyl]-6-(N-benzl-N-(2-bromoacetyl)-amino-quinazolin-4(3H)-one with N-Boc piperazine.

Pharmaceutical Formulations

A: Dry Filled Capsules Containing 50 mg of Active Ingredient Per Capsule

| Ingredient | Amount per capsule (mg) |
| --- | --- |
| 2-Propyl-6-(N-benzoyl-N-pentyl)amino)-3[(21-(tetrazol-5-yl)biphen-4-yl)methyl]-quinazolin-4(3H)-one | 50 |
| Lactose | 149 |
| Magnesium stearate | 1 |
| Capsule (size No. 1) | 200 |

The 2-propyl-6-(N-benzoyl-N-pentyl)-amino-3[(2'-(tetrazol-5-yl)biphen-4-yl)methyl]quinazolin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-propyl-6-(N-benzoyl-N-pentyl)amino-3[(2'-(tetrazol-5-yl)biphen-4-yl)methyl]-quinazolin-4(3H)-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide (25 mg) and 2-propyl-6-(N-benzoyl-N-pentyl)amino-3-[(2'-(tetrazol-5-yl)biphen-4-yl)-methyl]quinazolin-4(3H)-one (50 mg) pregelatinized starch USP (82 mg), microcrystalline cellulose (82 mg) and magnesium stearate (1 mg).

D: Suppository

Typical suppository formulations for rectal administration can contain 2-propyl-6-(N-benzoyl-N-pentyl)amino-3[(2'-(tetrazol-5-yl)-biphen-4-yl)-methyl]-quinazolin-4(3H)-one (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-propyl-6-(N-benzoyl-N-pentyl)amino-3-[(2'-(tetrazol-5-yl)biphen-4-yl)-methyl]quinazolin-4(3H)-one sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound or a pharmaceutically acceptable salt thereof selected from the group consisting of the compounds in the following table:

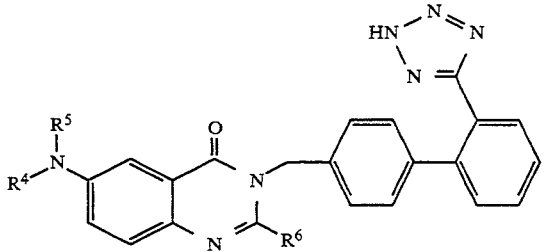

| R6 | R5 | R4 |
|---|---|---|
| n-butyl | COO-i-butyl | benzyl |
| n-propyl | COO-i-butyl | n-butyl |
| n-propyl | COO-i-butyl | n-propyl |
| n-propyl | COO-i-butyl | allyl |
| n-propyl | COO-i-butyl | n-pentyl |
| n-propyl | COO-i-butyl | n-pentyl |
| n-propyl | COO-i-butyl | (CH2)3-phenyl |
| n-propyl | COOCH3 | benzyl |
| n-propyl | COO-i-butyl | benzyl |
| n-propyl | COO-n-propyl | benzyl |
| n-propyl | COO-n-butyl | benzyl |
| n-propyl | COO-benzyl | benzoyl |
| n-propyl | COO-n-hexyl | benzyl |
| n-propyl | COO—(CH2)2OCH3 | benzyl |
| n-propyl | COOn-propyl | CH2-cHex |
| n-propyl | COOn-butyl | n-butyl |
| n-propyl | SO2n-butyl | benzyl |
| n-propyl | CON(methyl)n-propyl | benzyl |
| n-propyl | CON(methyl)ethyl | benzyl |
| n-propyl | CO-phenyl | n-pentyl |
| n-propyl | CO-benzyl | n-pentyl |
| n-propyl | CO-4-pyridyl | n-pentyl |
| n-propyl | CO-phenyl-4-Cl | n-pentyl |
| n-propyl | CO-phenyl-4-OCH3 | i-hexyl |
| n-propyl | CO-2-furoyl | n-pentyl |
| n-propyl | CO-morpholinyl | benzyl |
| n-propyl | CO-n-butyl | benzyl |
| n-propyl | CO-phenyl-4-F | n-pentyl |
| n-propyl | CO-phenyl-4-F | n-butyl |
| n-propyl | CO-phenyl-4-CH3 | n-pentyl |
| n-propyl | CO-phenyl-3-Br | n-pentyl |
| n-propyl | COO-i-butyl | methyl |
| n-propyl | CO-n-butyl | n-butyl |
| n-propyl | COO-ethyl | benzyl |
| n-propyl | CO-phenyl-4-CF3 | n-pentyl |
| ethyl(2-n-butyl) | CO-phenyl-4-F | n-pentyl |
| c-propyl | CO-phenyl | n-pentyl |
| ethyl(benzyl) | CO-phenyl | benzyl |
| c-propyl | CO-phenyl | benzyl |
| n-propyl | CO-4-pyridyl | n-butyl |
| ethyl | CO-phenyl | benzyl |
| n-propyl | CO-3-pyridyl | n-pentyl |
| ethyl | CO-phenyl | CO-phenyl |
| n-propyl | CO-phenyl-4-SCH3 | n-pentyl |
| n-propyl | CO-phenyl | n-propyl |
| n-propyl | CO-phenyl | (CH2)CHO |
| n-propyl | COCH3 | n-pentyl |
| n-propyl | CO-phenyl-4-F | n-propyl |
| n-propyl | CO-phenyl | i-butyl |
| n-propyl | CO-phenyl | (CH2)3CO2CH2CH3 |
| n-propyl | CO-phenyl | n-pentyl |
| n-propyl | CO-phenyl | CH2CO2CH2CH3 |
| methyl | CO-4-pyridyl | CH2CH=C(CH3)2 |
| n-propyl | CO-2-thienyl | n-pentyl |
| n-propyl | CO-2-thienyl | methyl |
| n-propyl | CO-4-pyridyl | (CH2)2OCH3 |
| n-propyl | CO-2-thienyl | ethyl |
| n-propyl | CO-phenyl-2-OCH3 | n-pentyl |
| n-propyl | CO-phenyl-4-Obenzyl | n-pentyl |
| n-propyl | CO-phenyl-4-Obenzyl | n-propyl |
| n-propyl | CO-phenyl-4-OH | n-pentyl |
| n-propyl | CO-phenyl-4-OH | n-propyl |
| n-propyl | CO-phenyl | CH2-2-pyridyl |
| n-propyl | CO-phenyl | CH2-2-pyridyl |
| n-propyl | CO-phenyl | CH2-4-pyridyll |
| n-propyl | CO-phenyl-4-OPO(Obenzyl)2 | n-pentyl |
| n-propyl | CO-phenyl-4-OH | n-butyl |
| n-propyl | CO-4-pyridyl | CH2-2-pyridyl |
| n-propyl | COphenyl-4-OPO(OH)2 | n-pentyl |
| n-propyl | COphenyl-4-OH | benzyl |
| n-propyl | CO-2-furoyl | CH2-2-pyridyl |
| n-propyl | CO-phenyl-4-OPO(ONa)2 | n-butyl |
| ethyl | COO-t-butyl | benzyl |
| ethyl | COO-benzyl | benzyl |
| n-propyl | COO-n-propyl | CH2-4-pyridyl |
| n-propyl | COO-n-propyl | CH2-3-pyridyl |
| n-propyl | O-n-propyl | CH2-2-pyridyl |
| CH2OCH3 | COO-n-propyl | CH2-2-pyridyl |
| n-propyl | COO-n-propyl | benzyl-4-NO2 |
| n-propyl | COO-n-propyl | benzyl-4-NH2 |
| n-propyl | COO-n-propyl | benzyl-4-N(CH3)2 |
| H | COO-i-butyl | methyl |
| ethyl | SO2-n-propyl | n-pentyl |
| ethyl | SO2-n-butyl | n-pentyl |
| ethyl | CONH-n-propyl | benzyl |
| n-propyl | CON(methyl)-i-propyl | benzyl-4-F |
| n-propyl | CO-phenyl-2-Oethyl | benzyl |
| n-propyl | CO-phenyl-4-Omethyl | benzyl-4-OCH3 |
| n-propyl | CO-phenyl | CH2-phenyl-4-OH |
| n-propyl | CO-phenyl-4-OH | CH2-3-pyridyl |
| n-propyl | CO-phenyl | CH2-phenyl-4-CO2CH3 |

2. The compound of claim 1 or a pharmaceutically acceptable salt thereof selected from the group consisting of the compounds in the following table:

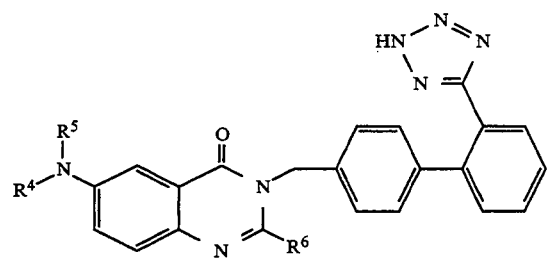

| R⁶ | R⁵ | R⁴ |
|---|---|---|
| n-propyl | SO₂-n-butyl | benzyl |
| ethyl | SO₂-n-propyl | n-pentyl |
| ethyl | SO₂-n-butyl | n-pentyl. |

3. The compound of claim 1 or a pharmaceutically acceptable salt thereof selected from the group consisting of the compounds in the following table:

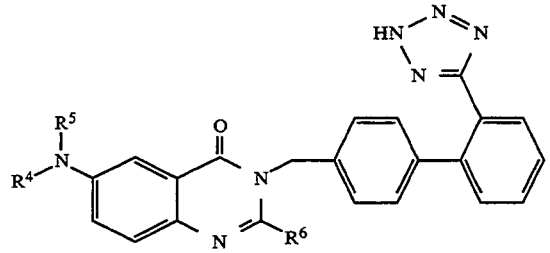

| R⁶ | R⁵ | R⁴ |
|---|---|---|
| n-propyl | CON(CH₃)-n-propyl | benzyl |
| n-propyl | CON(CH₃)ethyl | benzyl |
| n-propyl | CO-morpholino | benzyl |
| ethyl | CONH-n-propyl | benzyl |
| n-propyl | CON(CH₃)-i-propyl | benzyl-4-F. |

4. The compound of claim 1 or a pharmaceutically acceptable salt thereof selected from the group consisting of the compounds in the following table:

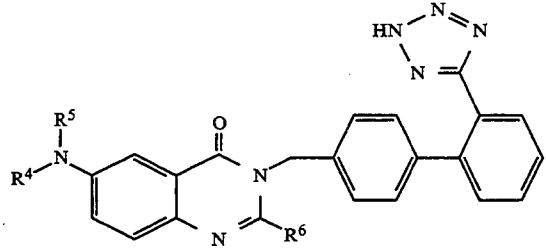

| R⁶ | R⁵ | R⁴ |
|---|---|---|
| n-propyl | CO-phenyl | n-pentyl |
| n-propyl | CO-benzyl | n-pentyl |
| n-propyl | CO-4-pyridyl | n-pentyl |
| n-propyl | CO-phenyl-4-Cl | n-pentyl |
| n-propyl | CO-phenyl-4-CH₃ | i-hexyl |
| n-propyl | CO-2-furyl | n-pentyl |
| n-propyl | CO-n-butyl | benzyl |

-continued

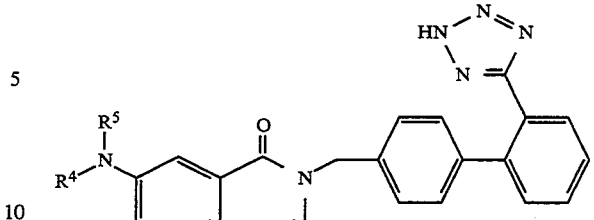

| R⁶ | R⁵ | R⁴ |
|---|---|---|
| n-propyl | CO-phenyl-4-F | n-pentyl |
| n-propyl | CO-phenyl-4-F | n-butyl |
| n-propyl | CO-phenyl-4-CH₃ | n-pentyl |
| n-propyl | CO-phenyl-3-Br | n-pentyl |
| n-propyl | CO-n-butyl | n-butyl |
| n-propyl | CO-phenyl-2-OCH₃ | benzyl |
| n-propyl | CO-phenyl-4-Obenzyl | n-pentyl |
| n-propyl | CO-phenyl-4-Obenzyl | n-propyl |
| n-propyl | CO-phenyl-4-OH | n-pentyl |
| n-propyl | CO-phenyl-4-OH | n-propyl |
| n-propyl | CO-phenyl | CH₂-2-pyridyl |
| n-propyl | CO-phenyl-4-OPO(Obenzyl)₂ | n-pentyl |
| n-propyl | CO-phenyl-4-OH | n-butyl |
| n-propyl | CO-4-pyridyl | CH₂-2-pyridyl |
| n-propyl | CO-phenyl-4-OPO(OH)₂ | n-pentyl |
| n-propyl | CO-phenyl-4-OH | benzyl |
| n-propyl | CO-2-furoyl | CH₂-2-pyridyl |
| n-propyl | CO-phenyl-4-OPO(ONa)₂ | n-propyl |
| n-propyl | CO-phenyl-4-F | n-propyl |
| n-propyl | CO-phenyl | i-butyl |
| n-propyl | CO-phenyl | (CH₂)₃CO₂CH₂CH₃ |
| n-propyl | CO-phenyl | CH₂CO₂CH₂CH₃ |
| methyl | CO-4-pyridyl | CH₂CH=C(CH₃)₂ |
| n-propyl | CO-2-thienyl | n-pentyl |
| n-propyl | CO-2-thienyl | methyl |
| methyl | CO-4-pyridyl | CH₂CH₂OCH₃. |

5. The compound claim 1 or a pharmaceutically acceptable salt thereof selected from the group consisting of the compounds in the following table:

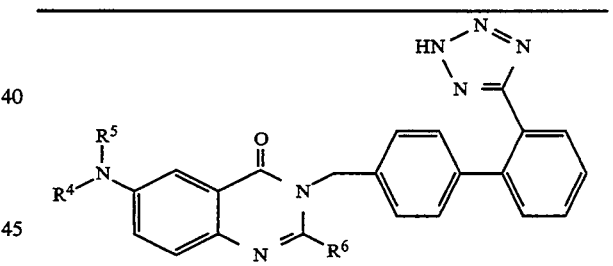

| R⁶ | R⁵ | R⁴ |
|---|---|---|
| n-butyl | CO₂-i-butyl | benzyl |
| n-propyl | CO₂-i-butyl | n-butyl |
| n-propyl | CO₂-i-butyl | n-propyl |
| n-propyl | CO₂-i-butyl | allyl |
| n-propyl | CO₂-i-butyl | n-pentyl |
| n-propyl | CO₂-i-butyl | (CH₂)₃phenyl |
| n-propyl | CO₂-methyl | benzyl |
| n-propyl | CO₂-i-butyl | benzyl |
| n-propyl | CO₂-n-propyl | benzyl |
| n-propyl | CO₂-n-butyl | benzyl |
| n-propyl | CO₂-benzyl | benzoyl |
| n-propyl | CO₂-n-hexyl | benzyl |
| n-propyl | CO₂—(CH₂)₂OCH₃ | benzyl |
| n-propyl | CO₂-n-propyl | CH₂-c-hexyl |
| n-propyl | CO₂-n-butyl | n-butyl |
| n-propyl | CO₂-ethyl | benzyl |
| ethyl | CO₂-t-butyl | benzyl |
| ethyl | CO₂-benzyl | benzyl |
| n-propyl | CO₂-n-propyl | CH₂-4-pyridyl |
| n-propyl | CO₂-n-propyl | CH₂-3-pyridyl |
| n-propyl | CO₂-n-propyl | CH₂-2-pyridyl |
| CH₂OCH₃ | CO₂-n-propyl | CH₂-2-pyridyl |
| n-propyl | CO₂-n-propyl | benzyl-4-NO₂ |
| n-propyl | CO₂-n-propyl | benzyl-4-NH₂ |
| n-propyl | CO₂-n-propyl | benzyl-4-N(CH₃)₂ |
| H | CO₂-i-butyl | CH₃. |

* * * * *